US005532351A

United States Patent [19]

Stefansson

[11] Patent Number: 5,532,351
[45] Date of Patent: Jul. 2, 1996

[54] NUCLEIC ACID SEQUENCES ENCODING OMGP

[75] Inventor: Kari Stefansson, Chicago, Ill.

[73] Assignee: Arch Development Corporation, Chicago, Ill.

[21] Appl. No.: 183,588

[22] Filed: Jan. 21, 1994

Related U.S. Application Data

[63] Continuation of Ser. No. 551,267, Jul. 12, 1990, abandoned.

[51] Int. Cl.$^6$ .......................... C07H 17/00; C12P 21/06; C12N 15/00
[52] U.S. Cl. .................. 536/23.5; 536/23.1; 536/24.31; 435/69.1; 935/1; 935/8; 935/11; 935/78
[58] Field of Search ................................. 536/23.1, 23.5; 536/24.31; 935/1, 8, 11, 78

[56] References Cited

PUBLICATIONS

Barker, D., et al., "Gene for von Recklinghausen Neurofibromatosis Is in the Pericentromeric Region of Chromosome 17," Science 236: 1100–1102 (1987).
Devereaux, J., et al., "A Comprehensive Set of Sequence Analysis Programs for the VAX," Nucleic Acids Res. 12:387–395 (1984).
Faissner, A., "Monoclonal Antibody Detects Carbohydrate Microheterogeneity on the Murine Cell Adhesion Molecule L1," Neurosci. Lett. 83:327–332 (1987).
Ferguson, M. A. J., "Cell–Surface Anchoring of Proteins Via Glycosyl–Phosphatidylinositol Structures," Ann. Rev. Biochem. 57:285–320 (1988).
Fisher, L. W., et al., "Deduced Protein Sequence of Bone Small Proteoglycan I (Biglycan) Shows Homology with Proteoglycan II (Decorin) and Several Nonconnective Tissue Proteins in a Variety of Species," J. Biol. Chem. 264:4571–4576 (1989).
Fountain, J. W., et al., "Physical Mapping of Translocation Breakpoint in Neurofibromatosis," Science, 244:1085–1087 (1989).
Gulcher, J. R., et al., "Two Large Glycolated Polypeptides Found in Myelinating Oligodendrocytes but not in Myelin," Proc. Nat. Acad. Sci. 83:2118–2122 (1986).
Ikezawa, H., et al., "Phosphatidylinositol–Specific Phospholipase C from *Bacillus cereus* and *Bacillus thuringiensis*," Methods Enzymol. 71:731–741 (1981).
Kruse, J., et al., "The J1 Glycoprotein—A Novel Nervous System Cell Adhesion Molecule of the L2/HNK–1 Family," Nature. 316;146–148 (1985).
Kruse, J., et al., "Natural Cell Adhesion Molecules and Myelin–Associated Glycoprotein Share a Common Carbohydrate Moiety Recognized by Monoclonal Antibodies L2 and HNK–1," Nature. 311: 153–155 (1984).
Kunemund, V., et al., "The L2/HNK–1 Carbohydrate of Neutral Cell Adhesion Molecules is Involved in Cell Interactions," J. Cell. Biol. 106:213–223 (1988).
Laemmli, U. K., "Cleavage of Structural Proteins During the Assembly of the Head of Bacteriophage T4," Nature. 227:680–685 (1970).

Le Beau, M. M., et al., "Evidence for Two Distinct c–src Loci on Human Chromosomes 1 and 20," Nature. 312:70–71 (1984).
Lichter, P., et al., "Delineation of Individual Human Chromosomes in Metaphase and Interphase Cells by In Situ Suppression Hybridization Using Recombinant DNA Libraries", Hum. Genet. 80:224–234 (1988).
Little, C., "Phospholipase C from *Bacillus cereus*," Methods Enzymol. 71:725–730 (1981).
Lopez, J. A., et al., "The $\alpha$ and $\beta$ Chains of Human Platelet Glyco–protein Ib are Both Transmembrane Proteins Containing a Leucine–Rich Amino Acid Sequence," Proc. Nat. Acad. Sci. 85:2135–2139 (1988).
Marton, L. S., et al., "Developmental Alterations in Molecular Weights of Proteins in the Human Central Nervous System That React with Antibodies Against Myelin–Associated Glycoprotein," J. Cell. Biol. 99:1642–1646 (1984).
McGarry, R. C., et al., "Recognition of Myelin–Associated Glyco–protein by the Monoclonal Antibody HNK–1," Nature. 306:376–378 (1983).
Mikol, D. D., et al., "A Phosphatidylinositol–linked Peanut Agglutinin–binding Glycoprotein in Central Nervous System Myelin and on Oligodendrocytes," J. Cell. Biol. 106:1273–1279 (1988).
Mikol, D. D., et al., "Developmental Changes in the Molecular Weights of Polypeptides in the Human CNS That Carry the HNK–1 Epitope and Bind *Phaseolus vulgaris* Lectins," J. Neurochem. 50: 1924–1928 (1988).
Norton, W. T., et al., "Myelination in Rat Brain: Method of Myelin Isolation," J. Neurochem. 21:749–757 (1973).
O'Connell, P., et al., "Fine Structure DNA Mapping Studies of the Chromosomal Region Harboring the Genetic Defect in Neurofibromatosis Type I," Am. J. Hum. Genet. 44:51–57 (1989).

(List continued on next page.)

Primary Examiner—Margaret Parr
Assistant Examiner—Bradley L. Sisson
Attorney, Agent, or Firm—Arnold, White & Durkee

[57] ABSTRACT

The present invention relates to a nucleic acid segment having a nucleotide sequence coding for oligodendrocyte-myelin glycoprotein (OMgp) which belongs to the CR-LR family of proteins. These molecular weight of the protein is about 120-kd as determined by gel electrophoresis. The protein is capable of being linked to biological membranes through a glycosylphosphatidylinositol lipid intermediate anchor. OMgp is expressed in the central nervous system and is correlated with myelination. This invention also relates to the purified OMgp, which bands at q11.2 of chromosome 17. OMgp maps in the chromosome within 6-kd of a translocation breakpoint t (1;17), which cosegregates with neurofibromatosis in some families. A recombinant vector incorporating the coding sequence for OMgp and a host cell for the vector are disclosed. Other aspects of the invention include disclosed methods for preparing the OMgp protein; the detection of the glycoprotein; as well as nucleic acid segments. Detection methods disclosed include in situ hybridization of the OMgp gene. The invention also relates to kits used to detect the OMgp or the nucleic acid coding for it in samples, for example in clinical samples such as blood. These kits and methods allow identification of persons, tissues or cells, including gametes, carrying the neurofibromatosis gene.

2 Claims, 20 Drawing Sheets

OTHER PUBLICATIONS

O'Connell, P., et al., "Two NF1 Translocations Map Within a 600–Kilobase Segment of 17q11.2," Science, 244:1087–1088 (1989).

Poltorak, M., et al., "Myelin–Associated Glycoprotein, a Member of the L2/HNK–1 Family of Neural Cell Adhesion Molecules, Is Involved in Nueron–Oligodendrocyte and Oligodendrocyte–Oligodendrocyte Interaction," J. Cell Biol. 105:1893–1899 (1987).

Rouleau, G. A., et al., "Flanking Markers Bracket the Neurofibromatosis Type 2 (NF2) Gene on Chromosome 22," Am. J. Hum. Genet. 46: 323–328 (1990).

Schmidt, M. A., et al., "Cases of Neurofibromatosis with Rearrangements of Chromosome 17 Involving Band 17q11.2," Am. J. Med. Genet. 28:771–777 (1987).

Shashoua, V. E., et al., "Demonstration of Glucuronic Acid on Brain Glycoproteins Which React with HNK–1 Antibody," Biochem. Biophys. Res. Commun. 138:902–909 (1986).

Szuchet, S., et al., "Maintenance of Isolated Oligodendrocytes in Long–Term Culture," Brain Res. 200:151–164 (1980).

VanTuinen, P., et al., "Regional Mapping Panel for Human Chromosome 17: Application to Neurofibromatosis Type 1," Genomics. 1:374–381 (1987).

Van Vactor, D., et al., "Analysis of Mutants in Chaoptin, a Photoreceptor Cell–Specific Glycoprotein in Drosophila, Reveals Its Role in Cellular Morphogenesis," Cell. 52:281–290 (1988).

Vicente, V., et al., "Isolation and Functional Characterization of the von Willebrand Factor–Binding Domain Located Between Residues $His^1$–$Arg^{293}$ of the α–Chain of Glycoprotein Ib," J. Biol. Chem. 263:18473–18479 (1988).

Ward, K., et al., "Diagnosis of Neurofibromatosis I by Using Tightly Linked, Flanking DNA Marker," Am. J. Hum. Genet. 46:943–949 (1990).

Mikol and Stefansson, *The Journal of Cell Biology*, vol. 106, Apr. 1988, pp. 1273–1279.

Mikol et al., *The Journal of Cell Biology*, vol. 110, Feb. 1990, pp. 471–479.

Mikol et al., *The Journal of Cell Biology*, vol. 111 (No. 6, Pt. 1), Dec. 1990, pp. 2673–2679.

```
  1 GTTCCGACTCTACAGAACAAGACGACCTTTAAGTTTCCCAGAGAAATGAGATGCTGATG            60

61 TTGAAGACGACACCACGGCTTTGATGGAATATCAGATATTGAAAATGTCTCTGCCTGT           120
                                            M  S  L  C  L

121 TCATCCTTCTGTTTCTCACACCTGNTATTTTATGCATTTGCCTCTCCAATGTATATGCA           180
     F  I  L  L  F  L  T  P  X  I  L  C  I  C  P  L  Q  C  I  C

181 CAGAGAGGCACAGGCATGTGGACTGTTCAGGCAGAAACTTGTCTACATTACCATCTGGAC           240
     T  E  R  H  V  D  C  S  G  R  N  L  S  T  L  P  S  G

241 TGCAAGAGAATATTATACACTTAAACCTGTCTTATAACCACTTTACTGATCTGCATAACC           300
     L  Q  E  N  I  I  H  L  N  L  S  Y  N  H  F  T  D  L  H  N

301 AGTTAACCCAATATACCAATCTGAGGACCCTGGACATTTCAAACAACAGGCTTGAAAGCC           360
     Q  L  T  Q  Y  T  N  L  R  T  L  D  I  S  N  N  R  L  E  S

361 TGCCTGCTCACTTACCTCGGTCTCTGTGGAACATGTCTGCTAACAACATTAAAC               420
     L  P  A  H  L  P  R  S  L  W  N  M  S  A  N  N  N  I  K

421 TTCTTGACAAATCTGATACTGCTTATCAGTGGAATCTTAAATATCTGGATGTTTCTAAGA         480
     L  L  D  K  S  D  T  A  Y  Q  W  N  L  K  Y  L  D  V  S  K

481 ACATGCTGGAAAAGGTTGTCCTCATTAAAAATACACTAAGAAGTCTGAGGTTCTCAACC          540
     N  M  L  E  K  V  V  L  I  K  N  T  L  R  S  L  E  V  L  N

541 TCAGTAGTAACAAACTTTGGACAGTTCCAACATGCCCTCCAAACTACATATCGTGG            600
     L  S  S  N  K  L  W  T  V  P  T  N  M  P  S  K  L  H  I  V
```

FIG. 1A

```
601  ACCTGTCTAATAATTCTTTGACACAAATTCTTCCAGTACATTAATAAACCTGACAAATC   660
      D  L  S  N  N  S  L  T  Q  I  L  P  G  T  L  I  N  L  T  N
661  TCACACATCTTTACCTGCACAACAATAAGTTCACATTCCAGACCAATCTTTTGACC     720
      L  T  H  L  Y  L  H  N  K  F  T  F  I  P  D  D  Q  S  F  D
721  AACTCTTTCAGTTGCAAGAGATAACCCTTTACAATAACAGGTGGTCATGTGACCACAAAC  780
      Q  L  F  Q  L  Q  E  I  T  L  Y  N  N  R  W  S  C  D  H  K
781  AAAACATTACTTACTGAAGTGATGATGAAAAGCCCATGTGATAGGACTC            840
      Q  N  I  T  Y  L  L  K  W  M  M  E  T  K  A  H  V  I  G  T
841  CATGTTCTACCCAAATATCATCTTTAAAGGAACATAACATGTATCCCACACCTTCTGGAT  900
      P  C  S  T  Q  I  S  S  L  K  E  H  N  M  Y  P  T  P  S  G
901  TTACCTCAAGCTTATTCACTGTAAGTGGGATGCAGACAGTGGACACCATTAACTCTCTGA  960
      F  T  S  S  L  F  T  V  S  G  M  Q  T  V  D  T  I  N  S  L
961  GTGTGGTAACTCAACCCAAAGTGACCAAATACCAAAACAATATGAACAAAGGAAACAA    1020
      S  V  T  Q  P  K  V  T  K  I  P  K  Q  Y  R  T  K  E  T
1021 CGTTTGGTGCCACTCTAAGCAAAGATACATCCACAGAGACTATCAATTCACATGAAGCAGCAGCTGATAAGGCTTTGTGC  1080
      T  F  G  A  T  L  S  K  D  T  T  F  T  S  T  D  K  A  F  V
1081 CCTATCCAGAAGATACATCCACAGAGACTATCAATTCACATGAAGCAGCAGCTGCAACTC  1140
      P  Y  P  E  D  T  S  T  E  T  I  N  S  H  E  A  A  A  T
1141 TAACTATTCATCTCCAAGATGGAATGGTCACAAACACAAGCCTCACTAGTCAACAAAT    1200
      L  T  I  H  L  Q  D  G  M  V  T  N  T  S  L  T  S  S  T  K
1201 CATCCCCAACACCCCATGACCCTAAGTATCACTAGTGGCATGCCAAATAATTCTCTGAAA  1260
```

FIG. 1B

```
           S  S  P  T  P  M  T  L  S  I  T  S  G  M  P  N  N  F  S  E
1261 TGCCTCAACAAAGCACAACCCTTAACTTATGGAGGAAGAGACAACCACAAATGTAAAGA    1320
       M  P  Q  Q  S  T  L  N  L  W  R  E  E  T  T  N  V  K
1321 CTCCATTACCTTCTGTGGCAAATGCTTGGAAAGTAAATGCTTCATTTCTTATTGCTCA    1380
       T  P  L  P  S  V  A  N  A  W  K  V  N  A  S  F  L  L  L
1381 ATGTTGTGGTCATGCTGGCTGTCTGAGGGTCTGCATTTTCTGAAACTAATGAAAGCACTC    1440
       N  V  V  M  L  A  V
1441 CTCCCTGATGTACAGTTGGGAAAATATGTCCATATCTAACCAGTGATTCGAGCTATATTT    1500
1501 AAGTATTCAAGAAGCCAGTCTTAACATTTCTAACTCTGATGTAAATGAAGTAACTTGTC    1560
1561 TTAAATAAAAAGAAATGCACAATGTCTTGGTACTTGCTGCTATTTTACTGTCTTAATTAAG    1620
1621 TAAACTAATGAGTTTCTTTTATAAAAAAATGAAATGTTTAAGGCTTCAATTTATTGCA    1680
1681 CAAAATATAAAAGCATCTAAACTTTAATATGTATTTATGTATGTTACACTGTCAAACAT    1740
1741 CTGGAAAATAAAGGTCTATGCTCAAAAAAAAAAAAAAAAAAAAAAAAAAAAAAAAAAAA    1800
1801 AAAAAAAA                                                       1808
```

FIG. 1C

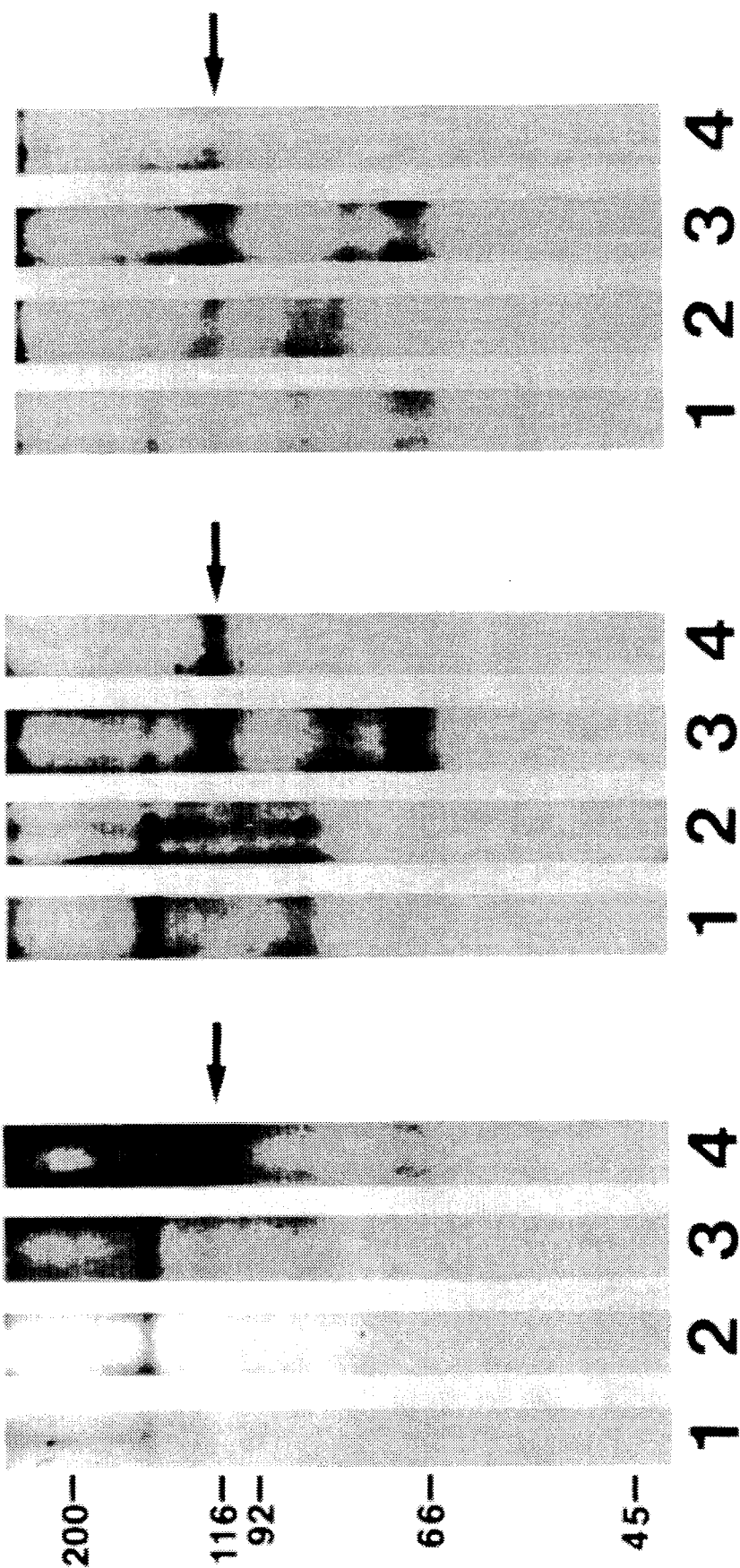

Ile-Cys-Pro-Leu-Gln-(His)-Ile-(His)-Thr-Glu-Arg-His-Arg-His-Val-Asp-Cys-Ser-Gly-Arg-Asp-Leu-Ser-Thr-(Leu)-Pro-Pro-Gly

N − TERMINAL EGF MOTIF

H₂N−I [C] P L Q [C] I [C] T E R H R H V D [C] S G R N L S̄ T L P S̄ G L Q E N

LEUCINE−RICH REPEATS

```
33  I I H L N L S Y N H F [T] D L H N Q L T Q Y T N
    L R T L L [D] I S [N] [R] L E S L [P] A H L P R S
    L W N Y L N S A A N N N I K L L [D] K S D T A Y Q W N
    L K Y L L L [D] V S K S M L E K V L I K N T L R S
    L E V I I L [N] L L N L W T V [P] T N M P S K
    L H T L Y L L H L L S L T Q I L P G T L I N L T N
    L Q E I T L Y N R W S * 204  L F T F [I] [P] D Q S F D Q L F Q
```

SERINE−THREONINE REPEATS

```
                                                    [P] T P       [P] T P
                                                 P Y P         P Y P
                                              K E H N M Y P T P  S [P] T P
                                     [T] K A H V I G . T . P C S T Q I S S L .      A F V .  S S P T P
205  C D H . K Q N [T] [T] L K W M M E . [T] [I] N S [L] .  [T] D K   N V K [T] P L
     [S G] F T . S S [L] F [T] V . S G M [Q] [T] V D . [T] F [T] S [T] D K
     . [S] V T . Q P K V T K [I] P K . . Q Y R . [T] [K] E [T] T F G A I [L] S K D T F T S T .
     E [D] T S T E T T . I N S H E A A A A . [T] I H L [Q] D G . M V T N . [S] L T S T .
     .     M T . L S [T] [I] S G . . . . [M] P N N F [S] E M P Q Q S T [L] N L W R E E T T .
```

C−TERMINUS

393  S V A N A W K V N − COOH

```
OMgp      1 -  I C P L Q C I C T E R H H V D C S G R N L S T . L P S G L Q E N - 32
Ibβ       1 - . C P A P C S C . A G T L . V D C G R R G L T W A S L P T I A F P D - 30
DECORIN  25 - . V C P F R C Q C . . H L R V Q C S D L G L D K . V P K D L P P D - 54
BIGLYCAN 25 - . M C P F G C H C . . H L R V V E C S D L G L K . S V P K T S P D - 54
```

FIG.9A

| | | | | | | | | | | | |
|---|---|---|---|---|---|---|---|---|---|---|---|
| L | xxL | dL | snN | xL | t | xL | p | xxxL | xxx | n | OMgp |
| L | xxxL | xL | xnN | kI | xx | VP | k | xxxF | xxx | x | Biglycan |
| L | xxxL | xL | xnN | kI | sx | Vxx | g | xfxx | xlk | x | Decorin |
| L | t | xxL | xL | sxN | xL | xx | LP | sxL | Fxx | x | N | dToll |
| L | r | xxL | DL | shN | xL | xx | IP | xdL | Fxx | xL | xx | dChaoptin |
| L | xxxL | xL | sxN | kI | xx | iP | xe | lxxL | xx | | yAdCyclase |
| L | r | xL | dL | sgN | xL | es | LP | pgL | Lqg | lp | q | LRG |
| L | t | xL | xL | sxN | xL | tt | LP | pgL | lda | lp | a | Ibβ |
| L | sxL | xL | sxN | xL | tt | LP | xG | llx | xlp | x | Ib |

NUCLEIC ACID SEQUENCES ENCODING OMGP

The government may own certain rights in the present invention pursuant to NIH grants 5 P01 HS-21442-03 and PHS 5 T32GM07281.

This application is a continuation of application Ser. No. 07/551,267, filed Jul. 12, 1990 now abandoned.

BACKGROUND OF THE INVENTION

1. Field of the Invention

The field of this invention relates generally to the family of CR-LR proteins, more specifically to the oligodenerocyte-myelin glycoprotein (OMgp). This invention also relates to the nucleic acid coding for the OMgp, and to segments thereof. Methods of producing the OMgp and the associated nucleic acid segments are also provided. Applications and advantages of the CR-LR protein family are presented. This invention also concerns methods to detect the OMgp and associated nucleic acid segments in specimens, such detection having as one goal to identify carriers of the neurofibromatosis gene on chromosome 17. Detection may be achieved by use of a kit.

2. Description of Related Art

A. Central Nervous System Proteins and Myelination

There are large numbers of proteins expressed in cells of the nervous system. Some of these are believed to participate in one of the major dramas of central nervous system development, myelination. Myelination is believed to involve complex interactions between oligodendrocytes and axons (Bunge, et al., 1978). Although the nature of these chemical and physical interactions has not been established, hypotheses have been proposed to explain certain portions of the myelination process. For example, Quarles has proposed that myelin-associated glycoprotein may mediate interactions between axons and myelin-forming cells (1984). Gulcher et al. (1986) relates a protein called gp 150/225 as having a similar role.

Central nervous system (CNS) myelin has a structure which is a complicated set of closely opposed oligodendrocytic membranes. Proteolipid protein and the myelin basic proteins are believed to contribute toward maintaining the opposition of compact myelin membranes, (Lemke, 1988), while the myelin-associated glycoprotein is believed to play a role in mediating the initial oligodendrocyte-neuron adhesion in periaxonal regions (Poltorak, et al., 1987).

What is known about the protein composition of myelin suggests that a few major proteins that account for most of the total protein. On a quantitative basis, there are minor proteins (Lees and Brostoff, 1984) whose functions are not known. One possible role for these minor proteins is to mediate interactions between oligodendrocytes and axons.

Proteins of the central nervous system may be associated with carbohydrates. Carbohydrates may be of functional significance by conferring specific properties on their associated proteins. (Sharon and Lis, 1982) Carbohydrates may also serve to identify proteins having specific functions. In this respect, carbohydrates are markers. An example of a protein which is postulated to play an important role in cell adhesion, and its carbohydrate component includes the HNK-1/L2 carbohydrate on the myelin-associated glycoprotein reported by McGarry et al., 1983. Carbohydrates also serve as markers for the neural cell adhesion molecule (N-CAM) (Kruse, et al., 1984), the $L_1$ glycoprotein (Kruse, et al., 1985), the $J_1$ glycoprotein (Kruse, et al, 1985), cytotactin (Grumet, et al., 1985), the neuron-glial cell adhesion molecule (Tucker, et al., 1984; Thiery, et al., 1985), and gp 150/225 (Gulcher, et al., 1986). These cells are likely to play important roles in cell adhesion.

B. Neurofibromatosis

One of the most common genetic diseases affecting the human nervous system is neurofibromatosis (NF) an inherited disease which is characterized by tumor formation in the nervous system. There are at least two clinically distinct forms of the disease, Type 1 (von Recklinghausen neurofibromatosis, incidence 1/3,000) and 2 (bilateral acoustic neurofibromatosis, incidence 1/100,000). Our discussion will focus on Type 1. NF1 primarily affects glial cells in the peripheral nervous system but can also affect glial cells in the central nervous syustem (CNS). The gene has nearly complete penetrance but highly variable expressivity and about 50% of cases are due to new mutations. The clinical features of neurofibromatosis include cafe-aulait spots, neurofibromas that increase in size and are the main cause of morbidity in the disease, iridial hamartomas (Lisch nodules), bone abnormalities, and learning disabilities. NF1 patients have an increased risk for developing optic gliomas as well as sarcomas which most often arise in proximity to plexiform neurofibromas. Depending on the location,number, and size of the tumors, those afflicted with NF may be disfigured, mentally retarded, or medically impaired. NF may be lethal.

The pattern of inheritance for NF is that of an autosomal dominant gene. That means that only one allele (condition of a gene) of a pair needs to be the NF gene to produce the disease. Males and females are at equal risk to inherit (carry) the gene. Families in which the gene is segregating will show affected members in successive generations.

The NF gene is not expressed in all carriers to the same degree. Because of the variable expressivity of the gene in causing the NF phenotype, some cases may go undetected. A rule of thumb is to look for cafe au lait spots in persons not obviously affected with tumors. Cafe au lait spots are pigmented patches of skin that occur in persons with the NF gene. However, cafe au lait spots are not specific for this disease. Clinical criteria for the diagnosis of NF1 have recently been agreed on by an NIH Consensus Panel (Barker et al., 1987). An examination is said to be positive for NF if there are two or more of the following features: six or more cafe au lait spots; two or more neurofibromas or one plexiform neurofibroma; freckling in the axillary or ingunal regions; optic glioma; two or more Lisch nodules (iris homartomas); a distinctive osseous lesion such as spheroid dysplasia or thinning of the long-bone cortex, with or without pseudoarthrosis; and a first degree relative who meets the above criteria for NF-1. These criteria are obviously not precise, in particular in pediatric patients. Another problem is that spontaneous mutations to NF1 will be underdetected or detected late, due to absence of a family history.

More accurate methods for the detection of persons who are at risk of NF1, but who do not show obvious symptoms such as tumor formation, are needed. It is important to diagnose such carriers because knowledge of whether or not they are carrying the gene may affect their reproductive choices. Also carriers should be monitored more than non-carriers for tumor growth to facilitate earlier surgical intervention and treatment. Prenatal testing for NF1 would also be possible if detection was not dependant on clinical symptoms.

C. Chromosomal Location of the Neurofibromatosis Gene

Some studies indicate that the NF1 gene is on chrosomome 17. Genetic linkage analysis has demonstrated that NF1 is the result of a mutation of a gene located in the proximal part of the long arm of chromosome 17. Further support for this localization was gained from the study of two unrelated families in which balanced chromosomal translocations involving chromosome 17 at band q11.2 segregate with the disorder. Although definitive proof is lacking, it is believed that these translocations directly involve and alter the NF1 locus (NF1). There have been some families with neurofibromatosis in which other chromosomal translocations cosegregate. By studying the cosegregation of these two characteristics, it was determined that their inheritance was correlated. One translocation was between Chromosomes No. 1 and 17. (A translocation results from breakage of at least 2 chromosomes with rejoining of the resulting segments in combinations not present originally.)

Further confirmation of the location of the NF1 gene came from in situ hybridization studies. In this method, nucleic acid probes are labelled with radioactive isotopes or fluorescent dyes, and applied to cells in metaphase, a stage of cell division in which the chromosomes are most readily visible under the microscope as entities. The concentration of the label indicate the region of the gene.

Problems Addressed by this Invention

There is an undisputed need for direct DNA-based testing for the NF1 mutation or its product to overcome the limitations of clinical diagnostic criteria. Ideally, the NF1 gene needed to be cloned and sequenced, although indirect tests by use of DNA markers associated with the NF1 gene are of some use. (Ward, et al., 1990; Rouleau, et al., 1990) Some information on application of markers is provided by mapping studies (O'Connell, et al., 1989), however, there are many limitations and inaccuracies using markers. One of the limitations of using markers to detect gene carriers is that at least 2 family members known to be affected must be available. These techniques, therefore, are not available for population screening for carriers of NF1. Improved methods of detection would find immediate use in genetic counseling, prenatal diagnosis, presymptomatic or asymptomatic diagnosis, and investigation of the mechanisms of genetic control of the disease to explore prevention and treatment of the clinical problems. This invention relates to a protein and its corresponding nucleic-acid sequences that have dramatic implications for diagnosing and understanding NF1.

SUMMARY OF THE INVENTION

Human central nervous system cells during development were analyzed by the inventor in order to identify molecules whose appearance and expression levels were correlated with developmental processes. Of specific interest were proteins that appear about the time of myelination and/or that exhibit levels of expression that are correlated with definable developmental stages. One of the proteins the inventor observed at the time of myelination was a glycoprotein.

This protein had a molecular weight of about 120-kd by gel electrophoresis. The protein bound to peanut agglutinin (PNA) and was present in CNS myelin. The invention described herein relates to the isolation, purification, characterization and utilization of this protein and of the nucleic acid sequences related to it.

This invention also relates to a nucleic acid segment having a nucleotide sequence which codes for a protein which comprises the following properties:

A. It has a molecular weight of about 120-kd as determined by gel electrophoresis;

B. It has a binding affinity for peanut agglutinin (PNA); and

C. It has a capability of linking to biological membranes through a glycosylphosphatidylinositol (GPI) lipid intermediate anchor.

The nucleic acid segment disclosed herein encodes a protein which comprises four structural domains. These domains form the basis of classification of the protein and demonstrate its relationship to other proteins. The domains comprise a cysteine-rich (CR) region which occurs at the NH2 terminus of the protein and a series of tandem, leucine-rich (LR) repeating amino acid segments. The nucleic acid segment is further defined as coding for a protein that comprises a cysteine-rich domain of about 32 amino acid residues in length and a leucine-rich domain of about 204 amino acid residues in length. The other two domains are a serine-threonine rich region and a hydrophobic segment at the C-terminus. The cysteine-rich and leucine-rich regions bestow on this protein membership in a family of CR-LR proteins which are characterized by similar structural regions. It is believed that the CR and LR regions are responsible for the cell adhesion mediated by these proteins. Indeed the capability of linking to biological membranes through a glycosylphosphatidylinositol (GPI) lipid immediate anchor has been demonstrated for the protein related in this invention. Other examples of proteins in this family are the $\alpha$ and $\beta$ chains of platelet glycoprotein Ib, biglycan and chaoptin.

The nucleic acid segment may be further defined as coding for a protein having an amino acid sequence comprising about 433 residues. The amino acid sequence of the protein is essentially that set forth in FIG. 1A, FIG. 1B, and FIG. 1C. The segment also codes for any biologically functional equivalent of the protein sequence shown in FIG. 1A, FIG. 1B, and 1C. Those skilled in the art will realize that other amino acid substitutions may be made without substantially affecting the basic structure of the protein. The nucleic acid segment comprises approximately 1,808 nucleotides and is capable of hybridizing to the sequence of FIG. 1A, FIG. 1B, and FIG. C or to its complement. Nucleic acid hybridization is based on the finding that two separate but complementary strands of DNA will reassociate under specific conditions to form a double strand (duplex, double helix). Specific conditions include temperature and pH. For the strands to hybridize, they must share a common, but not necessarily identical, DNA sequence. The degree of complementarity between the strands determines the stability of the newly formed hybrid. An embodiment comprises a DNA segment. Various levels of stringent conditions well known to those skilled in the art will be desirable depending on the desired degree of homologous criteria for hybridization. The nucleic acid segment also includes at least a hybridizing position of the nucleotide sequence of FIG. 1A, FIG. 1B, and FIG. 1C.

An exemplary embodiment of this segment would be a DNA segment having up to about one hundred nucleotides. Another embodiment would be a segment comprising of up to about sixty nucleotides. A still further embodiment would be a nucleic acid segment comprising up to about 25 nucleotides.

The nucleic acid segment coded protein also comprises a serine/threonine-rich domain of about 180 amino acid residues. This domain has sites capable of attaching to O-linked carbohydrates.

What is also claimed is a protein which is coded by the nucleic acid segments described herein. One specific embodiment of this protein has a specific amino acid sequence essentially as set forth in FIG. 1 or in a biological functionally equivalent thereof. This protein has a molecular weight of about 120-kd as determined by SDS gel electrophoresis. It has a binding affinity for peanut agglutinin. In fact, peanut agglutinin affinity extraction is one of the major methods of purification of this protein. This protein also is capable of linking to biological membranes through a glycosylphosphatidylinositol (GPI) lipid intermediate anchor. It is in this role that the protein is believed to have properties important for cell adhesion. It is also likely to affect mitotic rate. The protein is formed of four structural domains. There is a leader sequence of about 17 amino acids. Two of the most important domains are those comprising a cysteine-rich (CR) domain at the $NH_2$ terminus of the protein, and the domain of tandem leucine-rich (LR) amino acid segments.

Generally, the protein that is the subject of this invention refers to a protein which is about 433 amino acids long because this is the presently known approximate length. However, the invention does not preclude the preparation or use of shorter or longer peptides if the protein or peptide has similar biological activity, structure, and cross-reactive immunologic reactivity, for example as defined by rabbit polyclonal anti-serum period. Moreover, biological activity only requires a peptide which includes an active site. It is known that antigenic properties, defined as the ability to direct the formation of an antibody which will complex with the antigen, require only a segment of protein.

The protein also contains a serine/threonine-rich domain compromising about 180 amino acid residues with sites capable of attaching to the O-linked carbohydrates. The protein is further defined as having a polypeptide backbone of about 44.5 kd. The protein is further defined as a glycoprotein. A subpopulation of the protein is characterized by the occurrence of a HNK-1 carbohydrate epitope. This epitope is important because of interactions with cells. It is believed that the protein disclosed herein is capable of interacting with other proteins through its leucine rich domains.

Other properties of the protein includes the map location of the gene encoding it on chromosome 17. Specifically, the map location is to band q11.2 of chromosome 17. In this location the protein segregates with the t(1;17) in families characterized by the inheritance of neurofibromatosis (NF1, the gene for NF2 is believed to be on chromosome 22). In fact, the protein maps to a location within 6-kd of the translocation break point of t(1;17). That neurofibromatosis is a common genetic disease inherited as an autosomal dominant means that the disease appears in successive generations of families in which the gene is segregating. The carriers of the gene express it in varying fashions, ranging from the occurrence of large tumors in strategically located organs, a potentially lethal condition or one that leads to brain damage, to smaller tumors which perhaps cause only cosmetic disfigurement. At the other extreme are carriers whose genetic status as carriers is uncertain because they do not express any identifiable tumors. It has been found that cafe au lait spots may be the only indication of the presence of the NF gene in some carriers. These spots are small pigmented areas in the skin. The difficulty in determining a correlation between cafe au lait patterns and the presence of the gene is that cafe au lait spots have other etiologies. An NIH Consensus Panel (Barker et al., 1987) has agreed on clinical diagnostic criteria, but these less than precise standards create uncertainty for potential carriers in planning their reproductive strategies or seeking preventive or early surgical intervention and treatment. For example, a carrier may wish not to pass the gene on to descendants, hence may opt for adoption or if the carrier is a male, artificial insemination. Tests for genes in utero are also not reliable at the present time. Particularly serious problems arise in detecting carriers in the absence of a family history and in young patients who may not show expression of the gene due to its age-related effects. Another example for the need for carrier detection is that persons discovered early to be carriers of the gene may benefit from more frequent monitoring to detect tumors, perhaps leading to their removal before causing serious clinical problems.

The protein which maps to the area of chromosome 17 associated with the inheritance of neurofibromatosis has been extracted from central nervous system cells, for example, oligodendrocytes, and also from central nervous system myelin, suggesting an etiological, rather than merely a marker role, for the OMgp.

Other aspects of this invention are recombinant vectors which incorporate the nucleic acid segments referred to above, or biologically functional equivalents thereof. Recombinant vectors may be used to produce the protein commercially and may be used to produce copies of the protein or its biological equivalent. On that basis, preparation of the protein, or a biological equivalent protein as a product of the expression of transformed host cells prepared by genetic engineering techniques is well within the skills of those within the art. The recombinant vectors may also include RNA, cDNA or biologically functional equivalents thereof. In one embodiment, the nucleic acid segment included in the vector includes amino acids in the active portions of the protein as set forth in FIG. 1A, FIG. 1B, and FIG. 1C. In another embodiment, the entire coding segment is contained in the vectors. Recombinant vectors in isolated segments may variously include the basic peptide coding regions, coding regions bearing selected alterations or modifications in the basic coding region, or larger proteins comprising the entire coding region. In addition, due to codon redundancy, this aspect of the invention is not limited to the particular sequences shown in FIG. 1A, FIG. 1B, and FIG. 1C.

For the recombinant vectors, the protein encoding sequence is positioned adjacent to, and under the control of, an effective promoter which can be adapted for expression in either a procaryotic or eukaryotic host. The promoter may be a eukaryotic promoter, for example, SV-40.

Various eukaryotic vectors are well known to those skilled in the art and may be used for insertion of the nucleic acid segment, e.g. RCD, RCMV, RMSG. Many host cell-lines are available for the insertion of the vector, e.g. ATT-20, RIN. (Chicet et al, 1977; Adams et al, 1987, Severino et al, 1989; More et al, 1983).

The host cells preferably contain a eukaryotic promoter and a polyadenyalation signal at the position 3' of the carboxyl terminal amino acid. This promoter should be within a transcriptional unit of the encoded protein. The host cell may be a eukaryotic or procaryotic cell.

It is a further object of this invention to describe a method of preparing the nucleic acid segment coding for the family of CR-LR proteins. The method comprises the steps of identifying and isolating nucleic acids from a sample, preparing a cDNA by use of reverse transcriptase enzymes, using the well-known polymerase chain reaction to detect and amplify the conserved sequences within the catalytic site coding sequence of the cDNA, followed by amplification of homologous DNA fragments, and fractionation and isolation of the amplified cDNA. A source of the nucleic acid segment, in particular of RNA, comprises myelin. Other cells in which the protein is processed in the central nervous system are also sources. The inventors have used the rat, for example, as a non-human source.

Another method of preparing the nucleic acid segment as described in this application comprises obtaining nucleic acids from eukaryotic cells, for example, from central nervous system derived cells which may be human cells, amplifying the predefined sequences of nucleic acid, preparing recombinant clones which include the amplified nucleic acids and selecting a clone which comprises a desired nucleic acid segment in accordance with any claims described herein.

Antibodies may be specifically directed against the protein by standard methods. These may be monclonal antibodies or polyclonal antibodies. The protein may be identified in tissue or in vitro, for example, in cultured cells, by use of antibodies prepared against the protein. These antibodies may be labeled, for example, with fluorescent label. A method for detecting the protein in tissue samples would consist of preparing the antibodies capable of complexing with the protein. These need not be antibodies specifically directed toward the protein; one of the criteria is that they are capable of complexing with it. The samples would be then contacted with the antibody under conditions appropriate for formation of an antibody-protein complex. The presence of the complex would then be detected, leading to the inference that the protein was present in the sample. The samples may be clinical samples such as blood or amniotic fluid. Immunohistochemical analysis has been used to show that OMgp is present in the nodes of Ranvier, for example, and in myelin (FIG. 2).

Methods to prepare the nucleic acid segment or one substantially equivalent to the segment coding for the protein or its biological equivalent, comprise standard forms and methods as discussed in Maniatis, et al, 1982. Short peptides or short nucleic acid fragments which hybridize to the peptides may be prepared as probes. The length of the probes will be usually at least fourteen bases, but may be larger or smaller, assuming hybridization is achieved. Nucleic acids are incubated with the appropriate segment under conditions appropriate for the formation of specific hybrids. These hybrids are then detected. They may be detected by means of a label incorporated into the probe, for example a fluorescent label. The formation of such hybrids is indicative of the presence of complementary nucleic acid sequences. An illustrative example of identifying and detecting a nucleic acid segment in samples consists of preparing a probe which is capable of hybridizing to the nucleic acid segments substantially as set forth in FIG. 1A, FIG. 1B, and FIG. 1C and contacting the probe with the sample to be tested under conditions appropriate for the formation of hybrids. The probe nucleic acid hybrid is then detected. The presence of the hybrid indicates that the nucleic acid segment was present in the sample originally. The segment may be smaller than that shown in FIG. 1A, FIG. 1B, and FIG. 1C.

This invention is also directed to antibodies capable of hybridizing with the protein prepared in accordance with the disclosure herein. This antibody may be labeled and may be further defined as a monclonal antibody.

A method of preparing a protein from cells includes disrupting the cells, for example, by centrifugation, collecting the disrupted cells after centrifugation, and applying the collected disrupted cells sequentially to peanut agglutinin affinity extractions to purify the protein. The protein is recovered either from the pellet resulting from centrifugation or the supernatant. The method disclosed may use cells from the central nervous system which may comprise human cells. The method also relates to cells derived from a Schwannomna or from oligodendrocytes.

A method for detecting the chromosomal region which is associated with the expression of neurofibromatosis is described. This method comprises the following steps:

(a) preparing a nucleic acid probe for the segment described herein, as it exists in patients with neurofibromatosis;

(b) contacting cells with the probe; and (c) detecting the probe. The probe may be labelled, for example, by enzymatic incorporation of a radioisotope (e g., $p^{32}$) into a newly synthesized strand of DNA or RNA. The labelled probe will hybridize with homologous nucleotide sequences in nylon or nitrocellulose filter-bound target DNA, for example. Detection of the probe-target DNA hybrids is achieved by allowing the radioactive hybrids to expose x-ray films (a processed called autoradiography), or by quantitating the radioactivity using a scintillation counter. Probes tagged with a nonradiotive label are also within the scope of this invention. Sources of non-radioactive probes include FMC BioProducts (Chemi Probe Kit), Boehringer Mannheim Biochemicals, Genius System, Tropix Inc., Southern-Light Plus, and Sigma Chemical Co., (Sulfa Probe Kit). The cells to which the probe is applied may be cells in metaphase wherein chromosomes are distinct and readily identifiable. The probe may be then contacted on the metaphase cells leading to the determination of the presence of the region in chromosome 17 associated with the expression of neurofibromatosis.

Kits may be constructed which may be used for detecting the proteins which are disclosed in this invention. One embodiment of a kit includes a carrier that is compartmentalized to hold multiple containers, a first container which would include a quantity of antibody capable of complexing with the OMgp protein, and a second container containing the means for detecting the antibody-protein complex. In an illustrative embodiment of a kit, the antibody is labelled. More specifically, the label could be a fluorescent label. The antibody in the kit is further defined as being a monclonal antibody.

Another kit which may be used is one for detecting the nucleic acid segment prepared in accordance with the invention. This kit would comprise a probe capable of hybridizing with the nucleic acid segment described herein in a carrier being compartmentalized to hold multiple containers, a first container containing a quantity of the probe capable of hybridizing with the nucleic acid segment, and a second container including a means for detecting the probe-nucleic acid hybrid. In this kit the probe may be labeled, for example, with a fluorescent label.

One application of these kits is to detect human carriers for the region of chromosome number 17 which is associated with the inheritance of neurofibromatosis. A method for detecting these carriers is important because as previously discussed, not all carriers exhibit clinical signs indicative of the presence of the gene and, furthermore, the detection of carriers before expression of the clinical symptoms would facilitate diagnostic and therapeutic intervention. The method of detecting the carriers would be to obtain a sample from the person to be tested. This sample could be most easily done on blood or amniotic fluid. The procedures of the kit would be then applied to the sample. The determination would then be made whether or not the neurofibromatosis associated region is present in the person from whom the sample was obtained.

It is proposed generally that the invention disclosed herein will prove useful in screening clone banks to detect other members of the CR-LR family, more specifically, those expressed in the nervous system. Subsequent comparisons of the sequences may shed light on the evaluation of nervous system development. The invention is also useful in detecting and investigating neurological diseases.

Knowledge of the normal sequence of OMgp permits determination of mutant sequences, for example, that associated with neurofibromatosis. The carriers of these mutant sequences can be detected independent of clinical symptoms. This may be done by constructing a probe for the diagnostic segment, or by use of restriction length fragments which may differ in affect individuals if the mutation affects a restriction site. Nucleic acid amplification of diagnostic segments is used to obtain sufficient samples to test by applying a probe and checking whether hybridization occurred.

Kits may be provided in accordance with the present invention to allow for detection of members of the CR-LR family either in clinical samples, in specimens from non-human mammals, or in cultured cells. Such kits may include, for example, a polyclonal or monoclonal antibody and an immunodetection reagent. The antigen-antibody complex may be labelled, e.g., by a fluorescent label. The tissue contacted may be in the form of a histological or clinical specimen, a cell culture, or a cell suspension. For tissues wherein the protein is not expressed, kits for nucleic acid detection are required. Otherwise, detection of the protein or a segment thereof, may be performed by use of a kit or analogous methods.

The following terms are used herein:

Substantially purified is used herein to refer to DNA segments isolated free of their natural state, as they might be present in the genome of an organism. This term is intended to include such segments as they would exist after genetic engineering, for example, for insertion into a recombinant vector.

The term complementary used herein in connection with amino acid sequences, refers to amino acids or peptides that exhibit an attractive force toward each other. With respect to nucleic acid sequences, the term complementary refers to sequences having sufficient complementarity to allow specific cross-hybridization of nucleic acid strands under appropriate conditions.

Biologically functional equivalent. Functionally significant equivalence requires similarity in function of amino acid sequences, as well as about 40–60% amino acid sequence identity in important regions, for example, as found among related CR-LR proteins. The identity criteria could in some instances be satisfied by amino acid equivalents (Table I). This phenomenon enables a wide range of equivalent embodiments to be prepared from the disclosures herein. As used herein, the phrase biologically functional equivalent, referring to amino acids, refers to the fact that the invention contemplates that changes may be made in certain of the foregoing basic sequences without necessarily reducing or losing their proteolytic or structural identity. For example, the sequence can be altered through considerations based on similarity of charge, for example, acidity or basicity of the amino acid group, hydropathic index or amphipathic score. In general, these broader aspects of the invention are founded on the foregoing general understanding in the art, that certain amino acids may be substituted for other like amino acids without appreciable loss of the peptide's ability to bind and to be active. Examples of exemplary embodiments of amino acids and substitutions are shown in Table I. One or more amino acid residues within the sequence can be substituted by another amino acid of a similar polarity which acts as a functional equivalent. Substitutes for an amino acid within the sequence may be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic and glutamic acid.

TABLE I

| Original Residue | Exemplary Substitutions |
| --- | --- |
| Ala | Gly; Ser |
| Arg | Lys |
| Asn | Gln; His |
| Asp | Glu; Asn |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Leu; Tyr |
| Ser | Thr |
| Thr | Ser |
| Trp | Tyr; Phe |
| Tyr | Trp; Phe |
| Val | Ile; Leu |

The same expansion of nucleic acid sequences other than that shown in FIG. 1A, FIG. B, and FIG. C is within the scope of this invention. The sequence of FIG. 1A, FIG. B, and FIG. C can be altered by making these substitutions, additions or deletions to provide for functionally equivalent molecules. For example, the neurofibromatosis region may vary somewhat in different families. Due to the degeneracy of nucleotide coding sequences, other sequences which encode substantially the same amino acid sequence as depicted in Table I may be used in the practice of the present invention. Also, in genetic engineering, certain alternate codons may be preferred by bacterial hosts. Because of the nucleic acid code degeneracy, which means that more than 1 codon will code for a particular amino acid, a collection of nucleotide sequences representing all possible codon variations of FIG. 1A, FIG. 1B, and FIG. 1C are within the scope of this invention. The sequence illustrated in FIG. 1A, FIG. 1B, and FIG. 1C and its complement, is a specific embodiment.

Closeness of relation among proteins or peptides can be measured by comparison of amino-acid sequences. There are many methods of aligning sequences in protein, but the differences in methods are only manifest when the degree of relatedness is quite small. The methods described in the Atlas of Protein Sequence and Structure, entitled SEARCH and ALIGN, define relatedness. As is well known in the art, related proteins can differ in number of amino acids as well as in the identity of each amino acid along the chain. That is, there can be deletions or insertions when two structures are aligned for maximum identity.

Other definitions and terms used in this invention include:

A vector is a genetic element (a "replicon") to which other DNA segments may be attached, thereby bringing about replication of the attached segment. Examples include: plasmids, cosmids, chromosomes, viruses. Coding sequence refers to a nucleotide sequence that is transcribed (DNA-RNA) and translated (RNA-protein) into a polypeptide, either in vivo or in vitro.

Transcription, initiation, and termination sequences regulate DNA. They flank a coding sequence. Promoter sequences are initiators.

Substantial homology is said to occur when: 1) one amino acid sequence predicts a structure fundamentally similar and thereby generally biologically equivalent to another; 2) nucleotides coding for the amino acid sequence match over a defined length of the protein molecules (at least 40% or more). Sequences that are substantially homologous can be identified under conditions of a selected stringency. Defining appropriate hybridization conditions is within the skill of the art. (Maniatis, et al. 1982.)

An open reading frame is a series of codons without termination codons; the sequence is potentially translatable into proteins.

Conservative residues are "exemplary substitutes" as in Table I, i.e., chemically similar residues.

Consensus sequences are those that are similar among related members of a family.

BRIEF DESCRIPTION OF THE DRAWINGS

Other objects and advantages of the invention will become apparent upon reading the following detailed description and upon reference to the drawings in which:

FIG. 1. Nucleotide sequence of the overlapping clones and the deduced amino acid sequence of OMqp. The nucleotide sequence begins with 104 nucleotides of 5' untranslated sequence. The NH$_2$-terminal and potential COOH-terminal signal peptides are underlined. In the sequence of the mature polypeptide, the cysteines and the potential N-glycosylation sites are boxed. In the 3' untranslated sequence, the stop codon and polyadenylation signal are also boxed. Nucleotide No. 145 was ambiguous; in one clone it was G and in another it was A, leading to either glycine or aspartic acid at position 14 in the NH$_2$-terminal signal peptide. The segment which had previously been revealed by NH$_2$-terminal amino acid sequencing is overlined. FIG. 1A is presented on three panels designated FIG. 1A, FIG. 1B, and FIG. 1C.—therefor.

(FIG. 1A and FIG. 1B) Peroxidase-antiperoxidase staining of formalin-fixed paraffin-embedded sections of spinal cord with affinity-purified polyclonal rat antibodies against the OMgp. Myelin sheaths are intensely stained (arrows, FIG. 1A and FIG. 1B) while a neuron (arrowhead, B) is unstained.

FIG. 3. Peanut agglutinin (PNA) affinity staining of developmental CNS samples. FIG. 3 is presented on three panels designated FIG. 3A, FIG. 3B, and FIG. 3C. Tissue homogenates from (FIG. 3A) hemisphere, (FIG. 3B) cerebellum, and (FIG. 3C) spinal cord at various ages were separated on a Fairbanks 5.6% gel: (lane 1) 29-wk fetus (lane 2) 37-wk fetus; (lane 3) 7 months after birth; and (lane 4) adult. Numbers indicate the molecular mass standards and the arrows point to the OMgp. The standards are 200 kD, myosin; 116 kD, β-galactosidase; 92 kD, phosphorylase b; 66 kD, BSA; 45 kD, ovalbumin. It is of interest to compare the varying temporal appearance of the OMgp in each tissue. The OMgp migrates somewhat more slowly than the 116-kD marker.

FIG. 6 is presented on two panels designated FIG. 6A and FIG. 6B. (A) Silver and (FIG. 6B) PNA staining of the OMgp protein isolation steps from white matter pellet, separated on a 7.5% Laemmli gel. The 100,000 g supernatant of white matter pellet incubated (lane 1) without enzyme shows no OMgp, while the 100,000 g supernatant of the sample incubated (lane 2) with 100 mU/ml B. cereus PLC contains the releases OMgp, which is then concentrated by (lane 3) ammonium sulfate precipitation, and further purified in the 0.5 M D-galactose eluates of the (lane 4) first and (lane 5) second PNA-agarose extractions. Silver stain of the final product shows that the OMgp (arrows) can be purified to near homogeneity from the pellet (A, lane 5) of a white matter homogenate. Numbers indicate molecular mass standards for the silver-stained gel.

FIG. 7. NH$_2$-terminal sequence of the oMgp. The first 28 amino acid residues of the OMgp were determined by automated Edman degradation using a gas-phase sequenator and analysis of phenylthiohydantoin derivatives. Uncertain residues are indicated in parentheses.

FIG. 8. Domains of OMgp. The figure shows the four major domains of what is likely to be the mature OMgp. It begins with the CR that is directly followed by 7½ LRs, then 4½ ST repeats. The predicted amino acid sequence ends in a short COOH-terminal hydrophobic region which probably serves as a signal for GPI attachment that is cleaved during biosynthesis of OMgp, leaving some unknown residue at the COOH-terminal amino acid, possible asparagine (residue 401). The $NH_2$-terminal cysteines, as well as some of the sequence similarities within the LRs and ST repeats are highlighted. The two serine residues in the CR that may have been derived from ancestral cysteine residues are overlined. Note the high content of proline residues (underlined) within the LRs.

FIG. 9. The CR (FIG. 9A) and LRs (FIG. 9B) of OMgp FIG. 9A. (A) This figure shows portions of four polypeptides which are composed of a CR at the $NH_2$ -terminus with a contiguous series of LRs. Numbers refer to amino acid positions in the mature polypeptides. Sequence similarities are highlighted, accounting for conservative substitutions. Ibβ, the β chain of platelet glycoprotein Ib (Lopez, et al., 1988); Decorin and biglycan, two proteoglycans from bone (Fisher, et al., 1989). (FIG. 9B) This shows the consensus sequences of the LRs in OMgp and eight other proteins. dToll, the product of the Toll gene in Drosophila; dChaoptin, the product of the chaoptic gene in Drosophila; yAdCyclase, adenylate cyclase from yeast; LRG, the serum leucine-rich glycoprotein; IBα, the α chain of platelet glycoprotein Ib.

Figure 10:
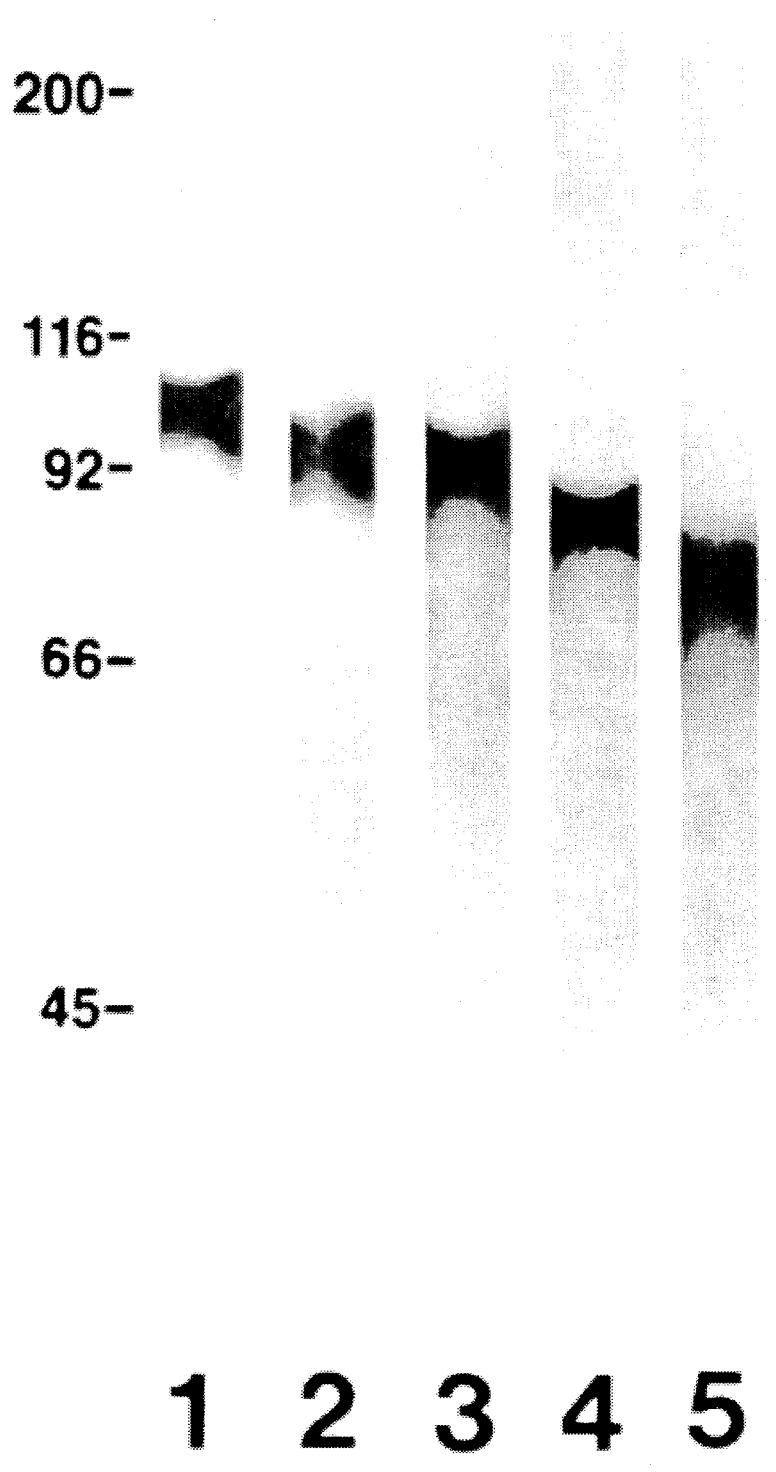

FIG. 10. Characterization of OMgp protein Carbohydrates. Enzymatic deglycosylation of the OMgp using (lane 2) neuraminidase, (lane 3) Endoglycosidase H, or (lane 4) Endoglycosidase F. Lane 5 represents deglycosylation with Endoglycosidase F followed by neuraminidase and then O-glycanase. Lane 1 represents the OMgp incubated without enzyme. The samples were separated on a 7.5% Laemmli gel, transferred to nitrocellulose, and stained with anti-OMgp antibodies. The polypeptide backbone of the OMgp protein is ~75 kD. Numbers indicate molecular mass standards.

FIG. 13 is presented on two panels designated FIG. 13A and FIG. 13B. An enriched sample of OMgp which had been purified by peanut agglutinin affinity chromatography was applied to an anion exchange column (MonoQ) and eluted with a NaCl gradient. Fractions were electrophoretically separated and the blots stained with either (FIG. 13A) mAb16, an anti-OMgp mAb, or (FIG. 13B) anti-HNK-1 mAb. The unbound fraction is shown in the far left lane, while fractions eluted at increasing NaCl concentration are shown in lanes 1–10: lane 1, 0.00–0.05M NaCl lane 2, 0.05–0.10M; lane 3, 0.10–0.15M; lane 4 0.15–0.25M; lane 5, 0.25–0.30M; lane 6, 0.30–0.35M; lane 7, 0.35–0.40M; lane 8, 0.40–0.60M; lane 9, 0.60–0.80M; lane 10, 0.80–1.00M. Staining of OMgp is indicated by arrows. Note that mAb16 stains OMgp mostly in lanes 3–8 and 10, whereas anti-HNK-1 mAb stains OMgp mostly in lanes 4–7, thus comprising a subset of OMgp molecules. Additional HNK-1 containing polypeptides of uncertain identity are found to elute in the 1.00M NaCl wash (B, lane 10).

DESCRIPTION OF THE PREFERRED EMBODIMENT

Figure 2A:
FIG. 2. Localization of OMgp protein using affinity-purified polyclonal antibodies.
(FIG. 2C) Culture of ovine oligodendrocytes (2 wk) stained with anti-OMgp antibodies using immunofluorescence.
(FIG. 2D) Attached cells after varying times in culture (5, 25 and 75 d; lanes 1–3) were washed, and the same total amount of protein was added per lane and separated on a 7.5% Laemmli gel. After separation the proteins were transferred to nitrocellulose, which was then stained with antibodies to the OMgp. The supernatant from the cells after 25 d was harvested, centrifuged at 100,000 g for 30 minutes, and the OMgp extracted by PNA affinity chromatograph (lane 4). It is clear that the amount of OMgp protein attached to the oligodendrocytes increases with increasing time in culture and it can be harvested from the supernatants. Numbers indicate molecular mass standards and the arrows point to the locations of the OMgp.
Figure 2B:

This invention is directed to a nucleic acid segment having a nucleotide sequence coding for a protein that is a member of a newly defined, previously unrecognized, family of proteins, the CR-LR family. "CR" refers to "cysteine-rich" and "LR" to "leucine rich." Based on the structure of the LR domain of these proteins, the proteins are expected to be capable of interacting with other molecules to enable cell adhesion. An embodiment of this invention was discovered among the quantitatively minor proteins of myelin. The existence of these proteins is well-recognized (Lees and Brostoff, 1984), but their functions and structures were previously unknown. Some are likely to be structural proteins, other regulatory.

Despite information on the presence of various proteins in the central nervous system, and of some data on the developmental stages of myelination, this complex phenomenon has not yet been unraveled. Uncovering these secrets of nervous system development is necessary for understanding both normal and abnormal development. Information of abnormal states will be helpful to the diagnosis, classification, and treatment of neural disease.

The OMgp protein discovered by the inventor is an embodiment of a quantitatively minor protein among those isolated from oligodendrocytes or other CNS structures. The expression of OMgp is correlated with the developmental stages of myelination. The protein was initially isolated and partially characterized from cells of the adult human central nervous system (CNS) by Mikol and Stefansson (1988) in the pursuit of polypeptides extracted from human CNS tissue homogenates that had been subject to electrophoresis (Mikol, et al., 1988).

The protein was present in the adult spinal cord, cerebellum and hemisphere, but showed regional variation in its developmental expression, suggesting a role in development of the CNS. For example, the protein was detected in fetal spinal cord at 29 weeks of gestation and in cerebellum at 37 weeks of gestation, but only a small amount was detected in the cerebral hemisphere 7 months after birth. (FIG. 3A, FIG. 3B, and FIG. 3C).

The inventor investigated these minor proteins of myelin, in particular, their variation during development. Molecular weight changes were observed as developmental stages progressed. A 120-kD protein appeared at the time of myelination. The protein is a glycoprotein, has an affinity for peanut agglutinin (PNA) and is present in central nervous system (CNS) myelin. The protein was isolated, characterized, and thereby termed "oligodendrocyte-myelin glycoprotein" (OMgp). Using SDS gel electrophoresis applied to tissue homogenates, the molecular weight was approximated as 120 kD. The OMgp appears in both the supernatant and the cell pellet from the homogenate. The latter is a membrane bound form which can be released from the membrane as a soluble 105-kD form by incubation with phospholipase C (PLC). This enzyme is a phospholipase which cleaves the PI linkage (phosphatidylinositol).

The OMgp protein was initially isolated by sequential PNA affinity extractions (PNA affinity chromatography).

The carbohydrate composition of OMgp was determined by its response to enzymatic treatments. The saccharide structure for which PNA is known to have the highest affinity usually resides on O-linked glycans (Pereira, et al., 1976). Neuraminidase, Endoglycosidase H or Endoglycosidase F treatment did not affect PNA binding. These results suggest the presence of an 0-linked carbohydrate which is not affected by these enzymes.

Determination of the amino acid sequence revealed approximately 433 residues organized into approximately four structural domains. These domains may be characterized as:

(a) a short, cysteine-rich ("CR") motif at the $NH_2$ terminus including approximately 28 amino acids;

(b) a series of tandem, leucine-rich repeats called "LR";

(c) a serine/threonine rich region that probably contains attachment sites for O-linked carbohydrates;

(d) a hydrophobic, COOH-terminal segment that is likely to be cleaved concomitantly with the attachment of lipids during the biosynthesis of OMgp.

Of these domains, the CR and LR regions place this protein in a previously unrecognized family the "CR-LR" proteins. A distinguishing feature of this family is the presence of both of these domains. Another possible identifying feature is the absence of introns.

The nucleic acid segment coding for this protein was isolated by standard methods (Maniatis. et al. 1982) and sequenced. An illustrative embodiment of the sequence is shown in FIG. 1A, FIG. 1B, and FIG. 1C. Because of the degeneracy of the genetic code, it is recognized by those skilled in the art that the scope of this invention covers biologically equivalent sequences to that shown in FIG. 1A, FIG. 1B, and FIG. 1C.

Figure 4:
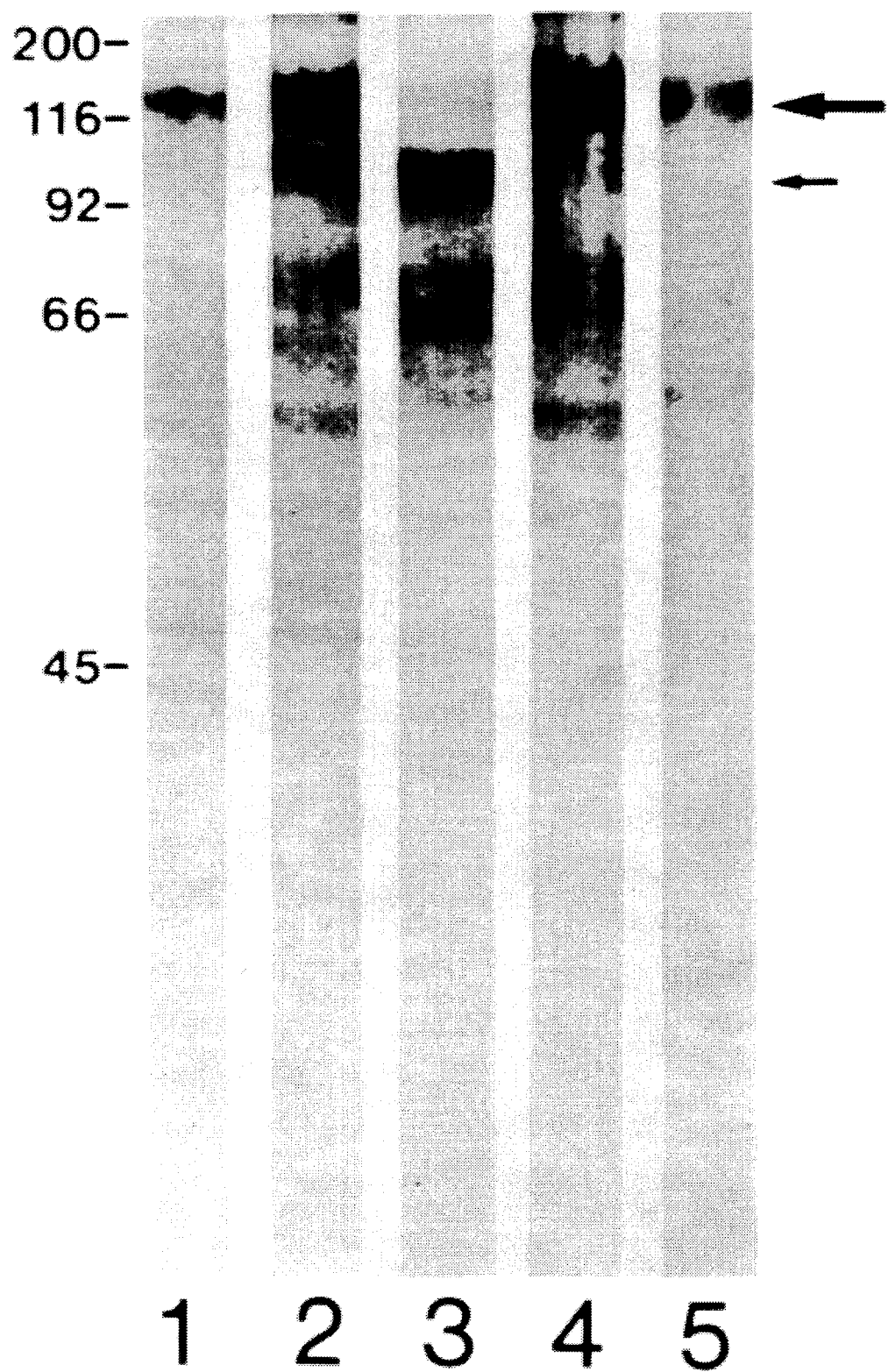
FIG. 4. Peanut agglutinin (PNA) binding to fractionated central nervous system (CNS) tissues. Equal amounts of total protein from (lane 1) crude gray matter, (lane 2) crude white matter, (lane 3) the 100,000 g supernatant from white matter, (lane 4) the 100,000 g pellet from white matter, and (lane 5) isolated myelin were separated on a 10% Laemmli gel, transferred to nitrocellulose, and stained with PNA. Numbers indicate molecular mass standards. The presence of two bands at 120 kD (large arrow) and 105 kD (small arrow) which partition into the pellet (120-kD band) or supernatant (105-kD band) is apparent. The OMgp is present in greater amount in white matter than in gray matter and there is more in the white matter pellet than in myelin.

More OMgp is present in the white matter than the gray matter of the central nervous system. The protein does not appear to be concentrated in compact myelin because there is less in myelin, isolated by the method of Norton and Podusto (1973), than in white matter. (FIG. 4).

Figure 5:
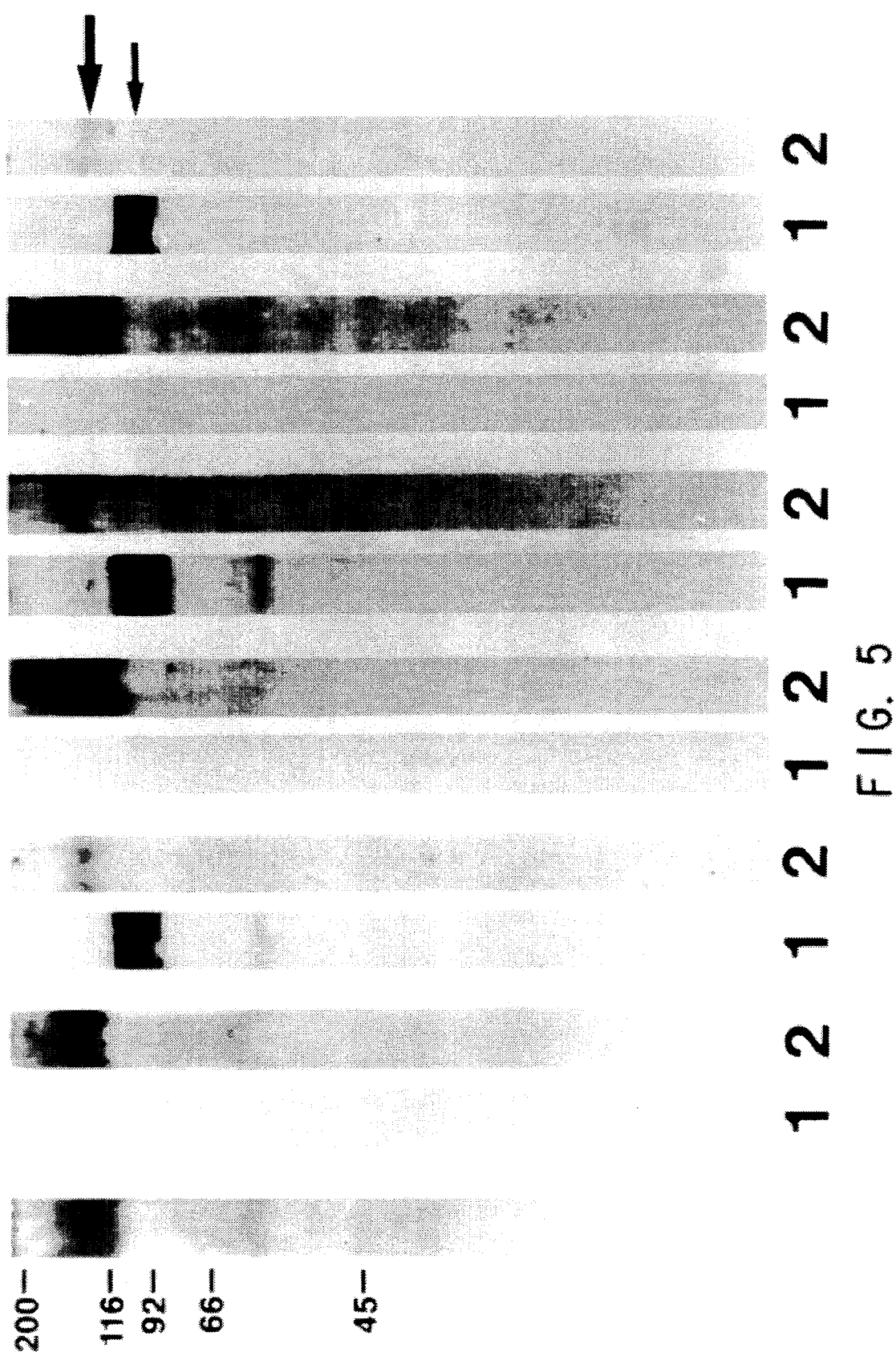
FIG. 5. Phospholipase C cleavage of the oMgp protein. White matter pellet was homogenized to 50 mg/ml (wet wt.). Equal aliquots of (A) this homogenate and of the (lane 0–1) 100,000 g supernatant and (lane 2) 100,000 g pellet of each incubation (B–G) were solubilized for SDS-PAGE on a 10% Laemmli gel, and subsequent PNA staining. (B) Incubation without enzyme: (C) incubation with 100 mU/ml Sigma B. cereus PLC alone (type III); (D) incubation in the presence of 5 mM Zn$^{++}$; or (E) 5 mM o-phenanthroline; (F) incubation with 10 U/ml Boehringer Mannheim B. cereus PLC (type I); (G) incubation with 50 mU/ml B. thuringiensis. Incubation without enzyme or with highly purified B. cereus PLC (Boehringer Mannheim) (PC-specific) does not release the OMgp, whereas a cruder preparation of B. cereus PLC (Sigma Chemical Co.) (PC-specific plus PI-specific) or purified B. thuringiensis PLC (PI-specific) cleaves most of the membrane-bound OMgp. Zn++, an inhibitor of the PI-specific PLC of B. cereus, blocks release of the OMgp while o-phenanthroline, an inhibitor of the PC-specific PLC of B. cereus, does not. The molecular mass difference between the two forms of the OMgp is readily apparent on this gel system (120-kD form, large arrow; 105-kD form, small arrow). Numbers indicate molecular mass standards.

In the initial steps of preparing OMgp by centrifugation of homogenized white matter (at 100,000 g), a 105 kD portion appeared in the supernatant, whereas a 120-kD form appeared in the pellet. The latter contained most of the protein. The pellet was solubilized in 1% NONIDET P-40™ (octylphenol-ethylene oxide condensate. The membrane-bound form may also be released as a soluble 105 kD form, by incubation with PI-specific PLC (FIG. 5). Embodiments using PLC comprise a relatively pure PI-specific PLC from *B. thuringiensis*. Another method to release the OMgp protein from membranes is a crude PLC preparation which contains both a PI-specific PLC and a PC-specific PLC (Sigma Chemical Co., Sundler, et al., 1978 a, b).

Zinc ($Zn^{++}$) an inhibitor of the PI-specific PLC of B. cereus (Ikezawa and Taguchi, 1981) blocks release of the OMgp protein, whereas O-phenanthroline, an inhibitor of the PC-specific PLC (Little, 1981) does not. There is no effect of a highly purified *B. cereus* PC-specific PLC (Boehringer-Mannhein Diagnostics, Inc.).

The HNK-1 carbohydrate, which has been shown to mediate adhesion between cells in the CNS (Kunemund, et al., 1988) is present on a subpopulation of OMgp molecules from human brain. The HNK-1 epitope contains a sulfated glucuronosyl residue (Shashoua, et al., 1986) which is probably attached to a complex N-linked triantennary oligosaccharide (Mikol, et al., 1988). In the CNS the HNK-1 carbohydrate may be a marker for adhesion molecules (Kruse, et al., 1985). It is of interest that a subpopulation of OMgp contains the HNK-1 carbohydrate. Heterogeneous expression of the HNK-1 carbohydrate has also been observed for other molecules and may allow for modulation of cell adhesion (Kruse, et al., 1984; Poltorak, et al., 1987; Faissner, 1987).

Whereas most of the OMgp elutes from an anion exchange column (Mono Q) between 0.1 and 0.6M NaCl and between 0.8 and 1.0M NaCl, with a peak at 0.15–0.35M NaCl as detected by staining with a mAb, against OMgp (FIG. 4A), the HNK-1 epitope is only present in the elutian between 0.15 and 0.4M NaCl with a peak at 0.25–0.35M NaCl (FIG. 4B).

Purification of the Protein

Either the supernatant or pellet of centrifuged homogenized cells may be used as a protein source. FIG. 6 presents results after two sequential PNA affinity extractions of a PLC supernatant which had first been concentrated by ammonium sulfate precipitation. PNA has a marked affinity for the protein which is eluted specifically by concentrations of D-galactose as low as 50 mM. D-galactose, but not D-glucose or α-methyl. D-mannoside binding of PNA to the protein on nitrocellulose was not blocked. These results indicate that PNA was binding to carbohydrate on the protein.

PNA has been shown to have the highest affinity for the structure gal [β1-3] gal Nac which is most often found on O-linked glycans (Pereira, et al., 1976).

Figures 6A, 6B:
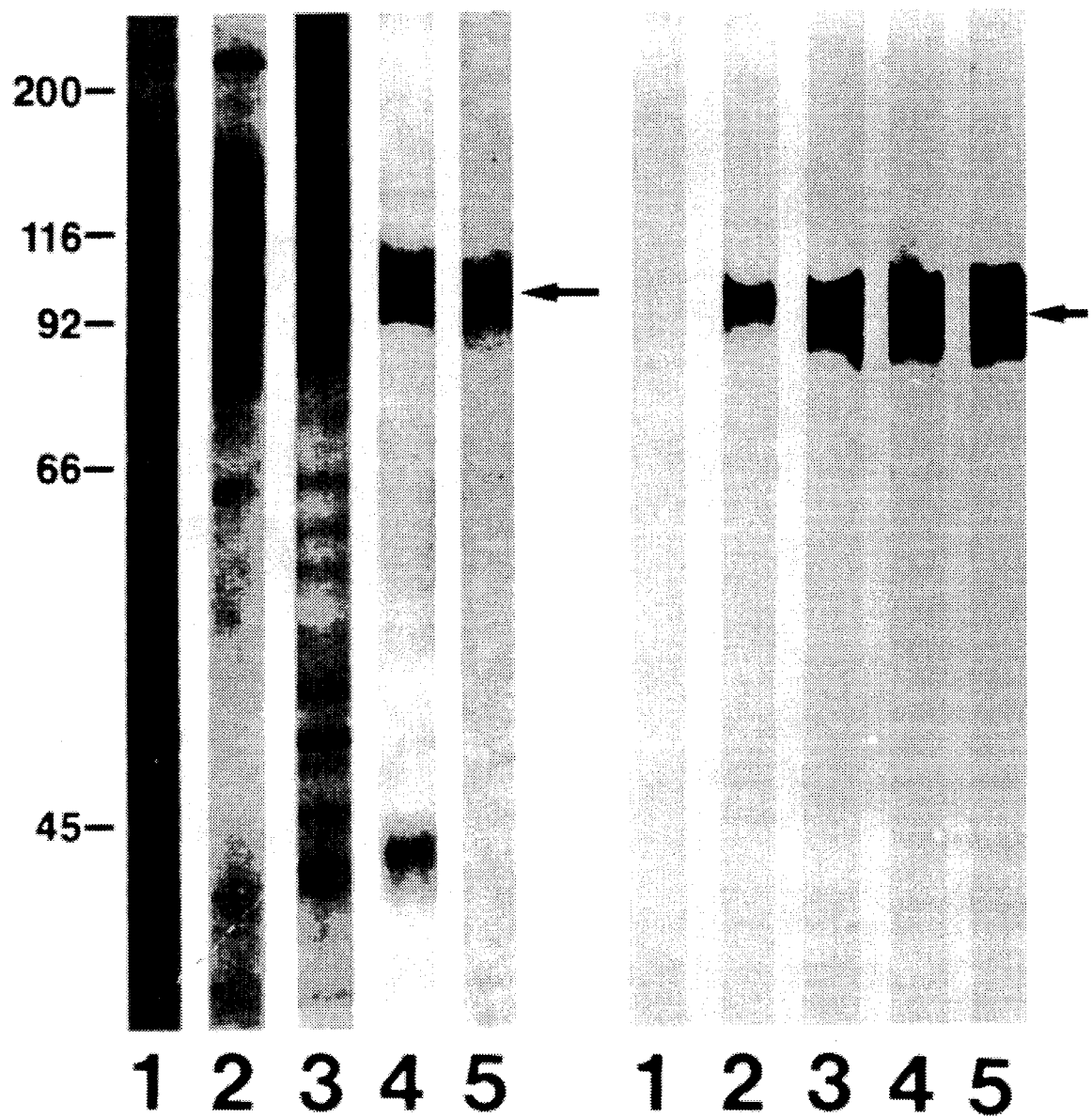
FIG. 6. Purification of the OMgp protein.

In FIG. 6A, and FIG. 6B results of treatment of the protein with a series of glycosidases to characterize contributions of its carbohydrate components to the approximate size of the protein. Sialic acids account for 10 kD, high-mannose N-linked glycans 15 kD, complex N-linked glycans 10 kD, and O-lined glycans ~5 kD. The supernatant yielded a 65 kD polypeptide in addition to the OMgp protein.

The presence of 2M NaCl in the wash buffer inhibits the nonspecific binding of most proteins to PNA-agarose but does not affect binding of OMgp.

The protein did not bind polyclonal antibodies against N-CAM, nor did the affinity-purified anti-OMgp antibodies bind to polypeptides with the relative mobilities of the larger two N-CAMs in brain homogenates.

The protein, isolated as the soluble 105-kD polypeptide was subjected to several enzymatic treatments in order to assess its carbohydrate composition. Neuraminidase cleavage of sialic acids resulted in a 95 kD polypeptide. Treatment with Endoglycosidase H or Endoglycosidase F yielded polypeptides of 90 or 80 kD, but PNA binding was unaffected, which suggested the presence of O-linked carbohydrates. When Endoglycosidase F cleavage of N-linked glycans was followed by incubation with neuraminidase and finally with O-glycanase, a 75 kD polypeptide was obtained that did not bind PNA.

PNA and anti-OMgp antibodies bound to 120 kD polypeptides in bovine, ovine and canine brains, bound weakly in mouse and rat brains, and did not bind in chicken brains. Quantitative versus qualitative interspecies differences require elucidation.

Location of the Protein as Shown by Immunohistochemical Staining

Figure 2C:
Figure 2D:
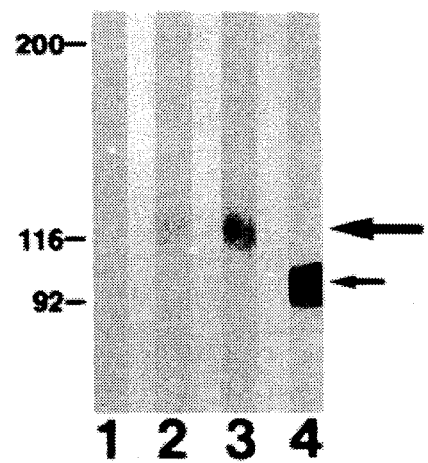

Affinity-purified polyclonal rat antibodies to OMgp stained the myelin sheaths on tissue sections from formation-fixed, paraffin-embedded human and ovine CNS (FIG. 2A, FIG. 2B, FIG. 2C, and FIG. 2D). Peripheral nervous system myelin and other CNS structures did not stain. Staining was observed also in the nodes of Ranvier. Immunoblot staining of polypeptides that had been subjected to electrophoresis from sheep white matter homogenate or sheep myelin, with either PNA or anti-OMgp protein antibodies, showed the presence of the OMgp protein, primarily in the membrane-bound form. When ovine oligodendrocytes kept attached to dishes in culture were solubilized and similarly stained, both the membrane-bound and soluble forms were seen, the latter of which was recovered from the supernatant using PNA affinity chromatography (FIG. 2D). Furthermore, the cultures of attached oligodendrocytes showed time-dependent OMgp protein expression. With decreasing time after attachment, more of the membrane-bound OMgp protein was found in washed oligodendrocyte pellets. Immunofluorescence staining of unfixed oligodendrocytes demonstrated that OMgp protein is on the surface of the cells and increases in density after attachment (FIG. 2C). The cultures used for these experiments contained only (>98%) cells that carried galactocerebroside on their surface. Double-labeling experiments showed that the same cells stained for both galactocereboside and the OMgp protein.

Primary Structure of OMgp

The $NH_2$ terminal sequence of the OMgp protein is shown in FIG. 7. The inventor has determined the complete primary structure of the human oligodendrocyte-myelin glycoprotein. The deduced amino acid sequence predicts a polypeptide of 433 amino acids which includes a 17-amino acid leader sequence and four domains (1) a short cysteine-rich motif at the $NH_2$terminus (CR); (2) a series of tandem, leucine-rich repeats (LRs); (3) a serine/threonine rich region; and (4) a hydrophobic COOH-terminal segment.

The second ST repeat of OMgp is truncated with only 23 amino acids as compared with ~40 in the other four.

The predicted COOH-terminus consists of a hydrophobic stretch of ~15 amino acids that is in keeping with the weak sequence requirements for attachment of proteins to GPI. The 3' untranslated part contains a stop codon, a polyadenylation signal, and a poly (A) tail (FIG. 8).

The. CR-LR Family

OMgp shares the first three of its four domains with the platelet glycoprotein Ib, which is responsible for the adhesion of platelets to the exposed subendothelium during hemostasis. Together with glycoprotein Ib and several other proteins, OMgp belongs to a family of proteins that contain both an $NH_2$-terminal cysteine-rich motif and an adjacent series of LRs.

OMgp is a membrane glycoprotein anchored in the outer leaflet of the membrane solely through a glycosylphosphotidylinositol (GPI) lipid intermediate. This mode of attachment places OMgp in a class of proteins with diverse functions. The GPI linking may give a protein several unique features: (a) high lateral mobility in the membrane; (b) rapid cleavage from the membrane by the action of a phospholipase; and (c) generation of physiologic mediators such as diacylglycerol upon phospholipase cleavage (Ferguson and Williams, 1988).

The $NH_2$-terminus contains four cysteines spaced in a manner similar to what is found in the epidermal growth factor (EGF) motifs, although the full EGF motif typically contains six or eight cysteines. These comparisons suggest that the role of OMgp may be either in adhesion or as a mitogen. The cysteine rich regions vary in their distribution in various polypeptides.

The 7½ LR's are similar to repeats that have been described in several other proteins including bone small proteoglycans I and II (Fisher, et al., 1989), and the α and β chains of platelet glycoprotein Ib (Lopez, et al., 1988).

Supporting a hypothesis that LR's mediate adhesion between the proteins containing the repeats and other molecules, is the chain of platelet glycoprotein Ib which has been shown to bind von Willebrand factor through a polypeptide fragment that includes the LR's (Vicente, et al., 1988). Also, loss of functional mutations in the chaoptic gene (Drosophila) causes membrane separation of adjacent photoreceptor elements (Van Vactor, et al., 1988).

OMgp is the only protein the inventor is aware of containing LR's that has been reported to be linked to membranes via a GPI moiety.

Enzymatic removal of both O-linked and N-linked glycans from OMgp have resulted in a polypeptide that binds the polyclonal antibodies but not peanut agglutinin, and measures ~52 kD. The characterization of the OMgp carbohydrate moiety is shown in FIG. 1. An O-linked carbohydrate is indicated.

Cloning of Human OMgp cDNA

Figure 11:
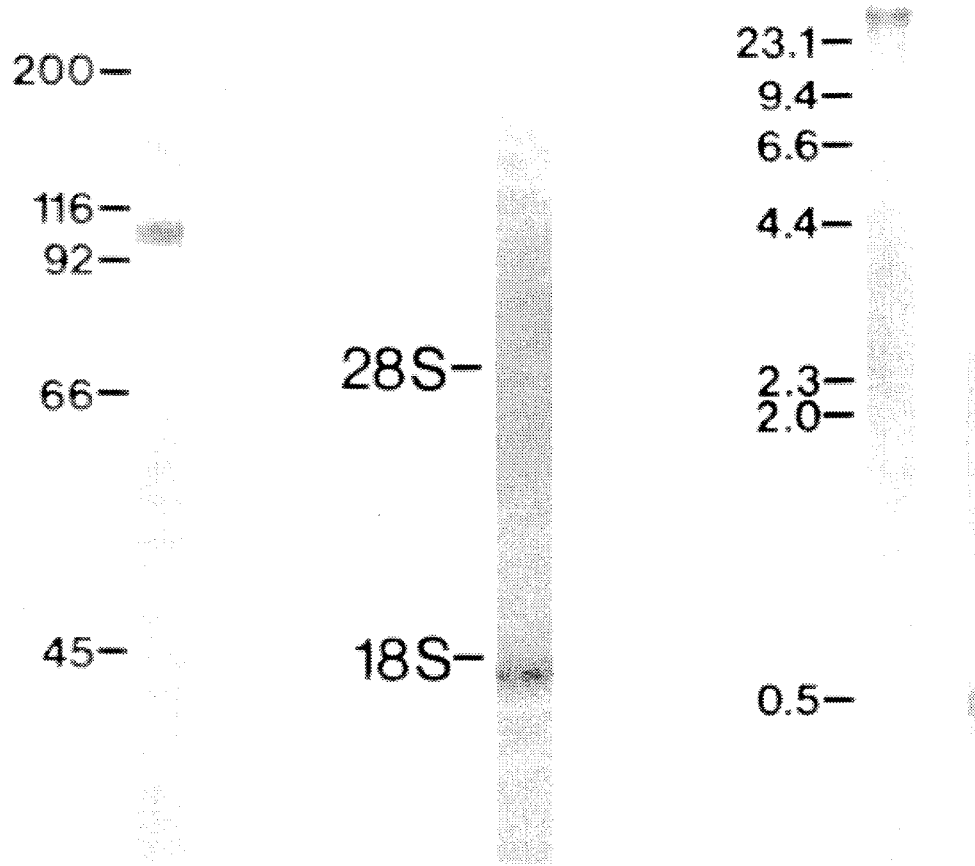
FIG. 11. Evidence that the cDNA clones encode OMgp (A), that OMgp is translated from a single mRNA (B) and that it is most likely transcribed from a single gene (C). Three lanes are shown after separation of purified human OMgp by SDS-PAGE. In lane (A) are the results of a Western blot to determine the molecular weight of the protein. The blot was stained with rabbit anti-OMgp polyclonal antibodies and shows staining of OMgp at 105 kD. The antibodies had been affinity purified on S1 fusion protein. Molecular mass standards in kD are shown along the left margin. Standards were myosin (200 kD); β-galactosidase (116 kD); phosphorylase b (92 kD); BSA (66 kD); ovalbumin (45 kD). Results of a Northern blot for RNA are shown in lane (B). 10 mg of total RNA from human white matter were probed with S1 cDNA after electrophoresis in 1.2% agarose with formaldehyde and capillary blotting. Standards are the positions of 28-S and 18-S ribosomal RNA bands. A distinct signal is apparent just below the level of the 18-S ribosomal RNA at ~1.8 kb. Lane (C) presents results of a Southern blot for DNA. Three lanes are within (C) each containing 5 mg genomic DNA from human peripheral blood lymphocytes. Three enzymes were used to cut the DNA: Eco-RI (lane 1), Taq I (lane 2), and Bam HI (lane 3). Each lane was probed with radiolabelled S1 cDNA. The results are a single band in each lane, shown in (C) with molecular size standards (kb) at the left.
Figure 12:
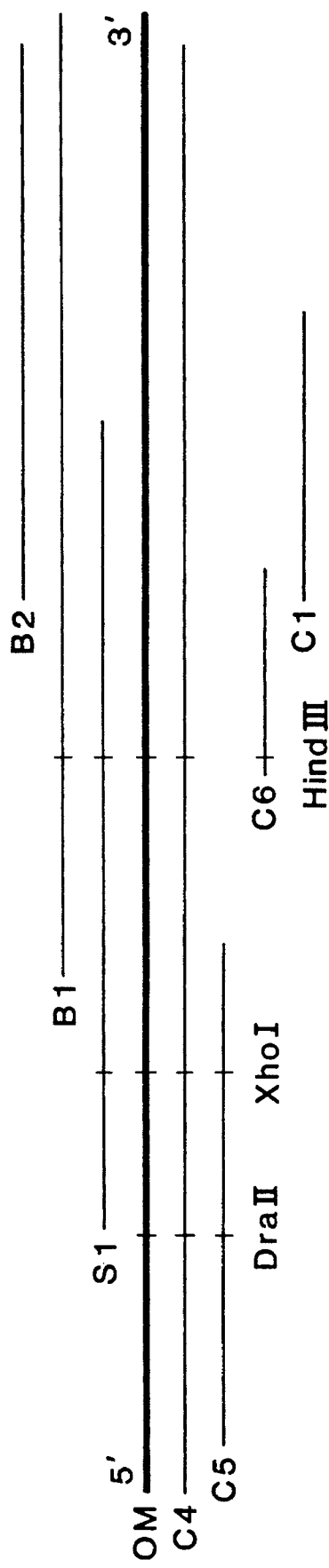
FIG. 12. Restriction map of OMqp cDNA clones. The positive clones from the three libraries (B, neonatal brainstem; S, neonatal spinal cord; and C, fetal spinal cord) are shown. Vertical lines mark three restriction endonuclease cleavage sites. Note that C4 is ~40 nucleotides short of the full-length composite, which is represented by the solid line and is marked OMgp.

Screening of a cDNA library prepared from human neonatal spinal cord using polyclonal rat anti-OMgp antibodies yielded a single positive ~1-kb clone designated S1. Supporting the contention that the S1 clone encoded OMgp, rabbit polyclonal antibodies were affinity purified on nitrocellulose replicas of plates containing lysed *E. coli* expressing S1 fusion protein. The S1 affinity-purified antibodies bound to purified OMgp on Western blots (FIG. 11A). When total RNA from human white matter was probed with S1 cDNA, a single ~1.8-kb band was observed (FIG. 11B). A Southern blot containing human genomic DNA cleaved with any of three restriction endonucleases was probed with S1 cDNA, and only one band was revealed in each case (FIG. 11C), indicating that there is probably only one copy of OMgp in the haploid human genome. The S1 clone was fully sequenced in both directions, and was used to reprobe the neonatal spinal cord library, as well as to probe a neonatal brainstem library and a fetal spinal cord library. The neonatal spinal cord library yielded no new clones, while the neonatal brainstem library gave two clones, B1 and B2. Screening of the fetal spinal cord library gave several positive clones (C1, C4, C5, C6). All of the clones obtained were restriction mapped, and formed ~1.8 kb of overlapping cDNA (FIG. 12), which is in good agreement with the mRNA size seen on Northern blot analysis. When Northern blots containing RNA from other tissues were examined with the same probes, nothing hybridized. Western blots containing electrophoresed proteins from several tissues were stained with the affinity-purified antibodies. Only in the CNS was there a polypeptide that bound the antibodies, which is in keeping with previous descriptions of the distribution of OMgp (Mikol and Stefansson, 1988).

Figure 13A:
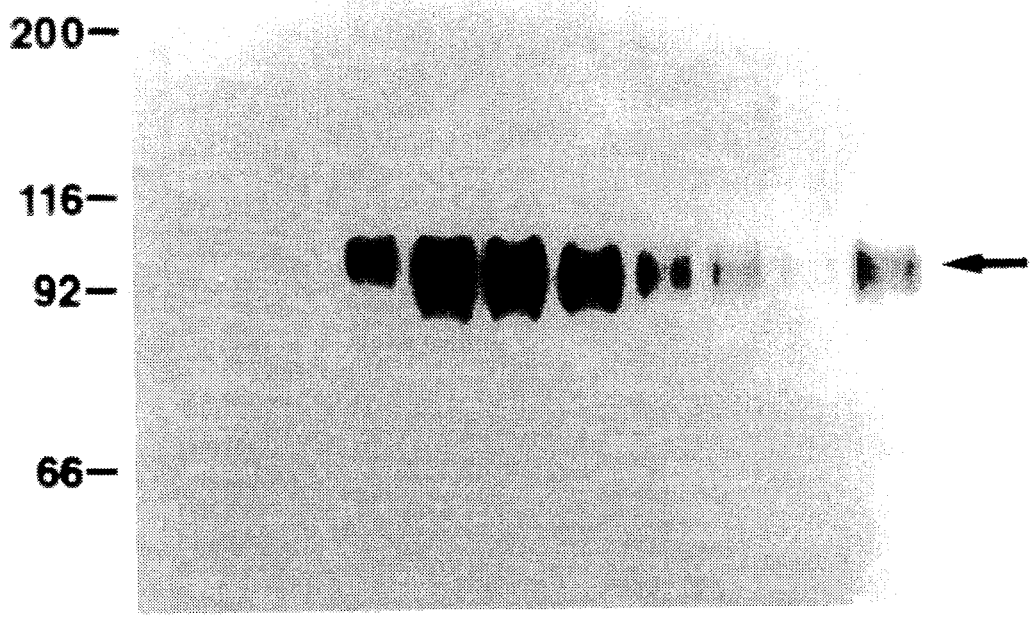
FIG. 13. Western blots containing OMgp eluted from an anion exchange column.
Figure 13B:
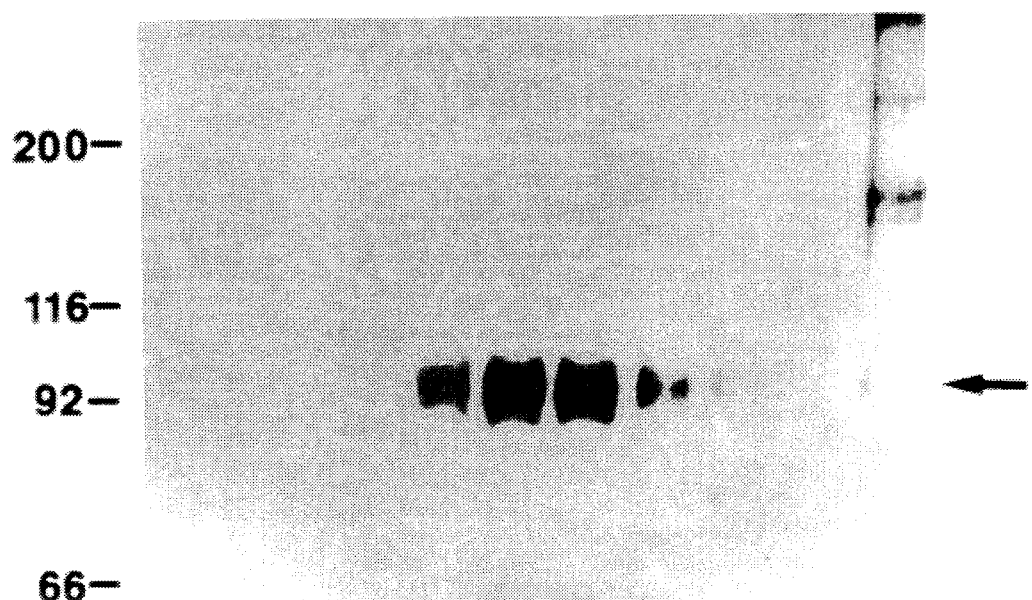

Evidence that OMgp contains the HNK-1 carbohydrate epitope is shown in FIG. 13A, and FIG. 13B. In FIG. 13A, mAb against OMgp reveals the elution of most of OMgp from an anion exchange column. However, as shown in FIG. 13B, the HNK-1 epitope is only on a subpopulation (see details in FIG. 13A and FIG. 13B legend).

Chromosomal Localization of the OMgp Gene

Figure 14:
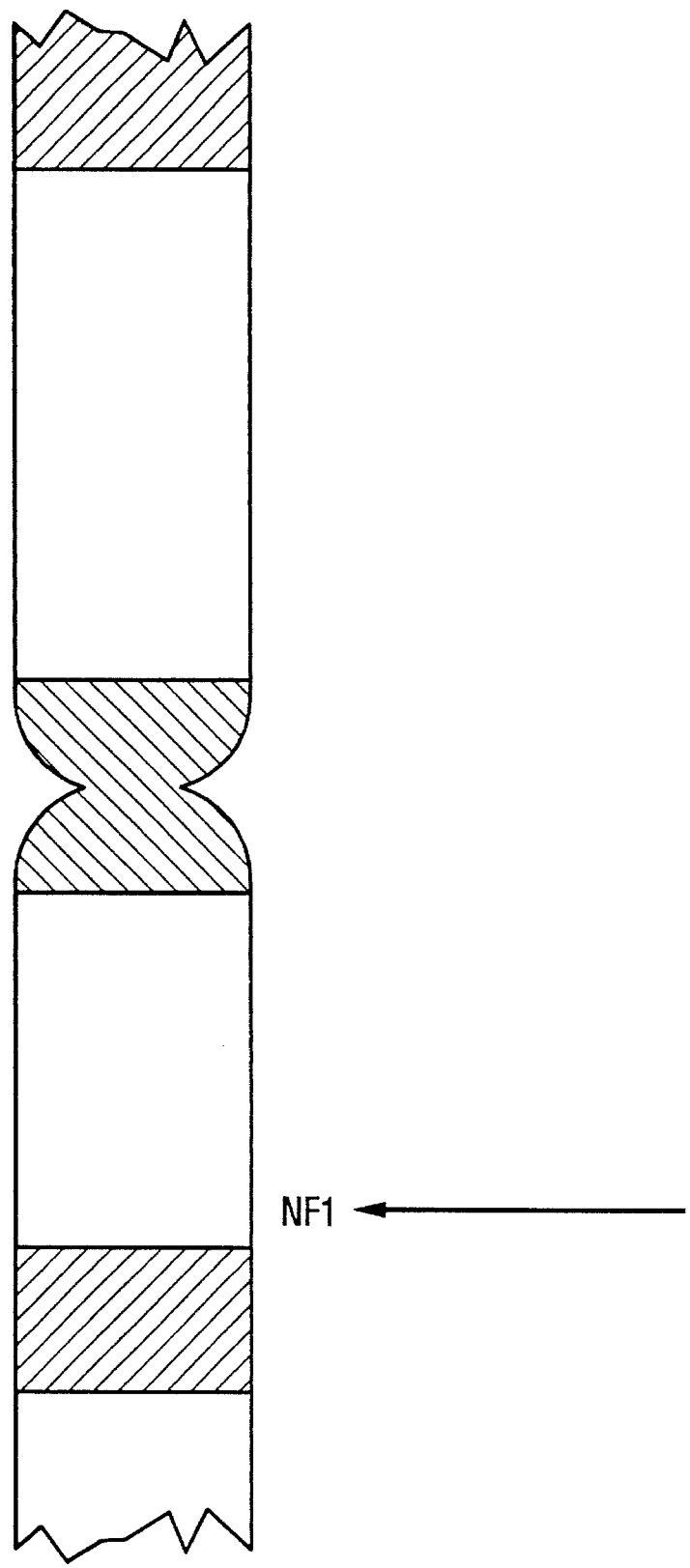
FIG. 14. A map showing the chromosomal location of the neurofibromatosis type I(NF1) mutation on the proximal part of the Long arm of chromosome 17. In families in which a balanced translocation between chromosomes Nos. 1 and 17, it was determined by cosegrative that the gene is an NF1 No. 17. A more specific localization was made to band q11.2.

Genetic linkage studies have indicated that NF1 is results of a mutation of a gene located in the proximal part of the long arm of chromosome 17. (FIG. 14).

The OMgp gene was localized by hybridizing a radiolabelled 12 kb genomic probe (M5E10, see FIG. 15) to human chromosomes from individuals who are apparently normal. (Le Beau, et al., 1984, Nature 312:70-71 presents the in situ hybridization techniques incorporated herein by reference). Hybridization resulted in a specific labelling only of chromosome 17, bands q11–12 (FIG. 16), the same area to which the NF1 gene had been localized.

To determine whether the OMgp gene is in the vicinity of either of the NF1-associated translocation breakpoints, pulse field gel electrophoresis was used. Fountain, et al. previously published a long-range restriction map of the region of the breakpoints. A probe used in that study, 17L1A, which detects rearrangements in DNA from patients in the family with the t(1;17)(p34.3;q11.2) translocation, recognizes a 290 kb Not I fragment and a 290 kb Sac II fragment in normal DNA. An OMgp cDNA probe, S1 (FIG. 5), also recognized Not I and Sac II fragments in this size range in DNA from human lymphoblastoid and leukemic cells without rearrangements of chromosome 17. These results indicate that 17L1A and S1 hybridize to genomic sequences that are physically linked.

Figure 17:
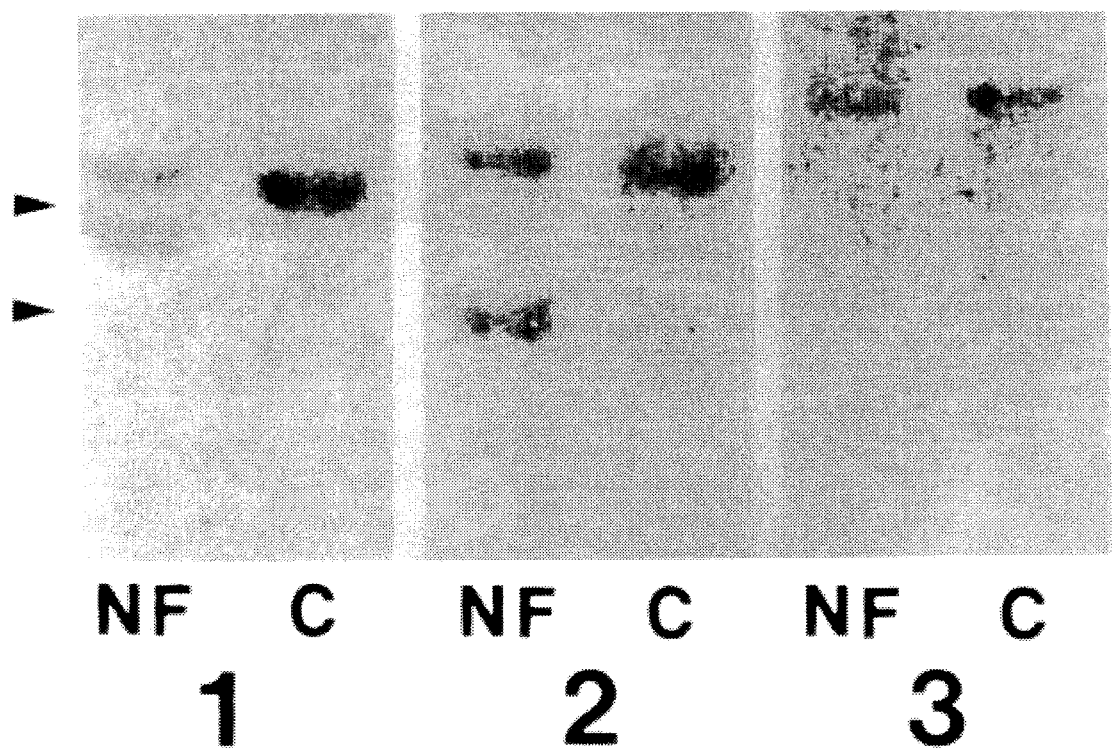
FIG. 17. A Southern blot with DNA from a lymphoblastoid cell line from an NF1 patient with a t (1;17) (NF) and normal human DNA (c). The blot was cut with PstI, Eco-RI, ScI or and probed with S1, a partial cDNA clone for OMgp. In each case, one abnormal fragment in addition to the restriction fragments detected in DNA from a large group of normal individuals, was observed. The arrow-heads serve as markers for size 9.5 kb and 6.6 kb respectively. There is an additional band in all of the Nf lanes corresponding to the abnormal allele. The smallest abnormal band was a 6 kb Eco-RI fragment, corresponding to the largest possible distance between the OMgp gene sequences contained in S1 and the breakpoint. A new Eco-RI site has been created by the chromosomal rearrangement.

A lymphoblastoid cell line from an NF1 patient with the 1;17 translocation was confirmed, by cytogenic analysis, to contain the translocation. When a Southern blot with DNA from the cell line cut with SacI, EcoRI or Pst I was probed with S1, in each case one abnormal fragment was observed in addition to the restriction fragments detected in DNA from a large group of normal individuals (FIG. 17). The smallest abnormal band was a 6 kb EcoRI fragment, corresponding to the largest possible distance between the OMgp gene sequences contained in S1 and the breakpoint.

Biotin-labelled M5E10 genomic probe was hybridized to metaphase cells from the cell line and specific labeling of the normal chromosome 17 homologue and the rearranged chromosome 1, was obtained but not of the rearranged chromosome 17. These results suggest that most or all of the segment corresponding to M5E10 is translocated to chromosome 1.

Chromosomal localization of the OMgp gene using fluorescent in situ hybridization with a biotin-labelled M5E10 probe.

Specific labelling of 17q11 was observed on one (in 3 cells) or both (in 17 cells) of chromosome 17 homologues in each of 20 cells examined. Signal was not detected on other chromosomes. Use of a panel of rodent-human hybrids also localized the OMgp gene to human chromosome 17.

EXAMPLES

Example 1

Synthetic Production of OMgp

In certain embodiments, OMgp or segments thereof may be prepared in accordance with the invention by non-recombinant synthetic recons by chemical synthesis or by use of a commercially available synthesizer, e.g., Applied Biosystems. This is usually only feasible for segments of about 40 amino acids.

Due to practical limitation on the size of nucleotides that can readily be prepared synthetically, such chemical synthetic preparation techniques will likely find their greatest utility in the preparation of segments for use as hybridization probes.

For certain applications, e.g., where larger nucleic acid polymers are required, it may be advantageous to prepare suitable nucleic acid polymers by recombinant techniques. The most preferred approach is cDNA cloning in that a nucleic acid molecule is obtained having a transcription unit that does not require RNA splicing of the subsequent RNA transcript. With OMgp, there appear to be no introns, however, so the cDNA and native DNS appear equivalent. This characteristic, of course, allows one to employ prokaryotic hosts for recombinant production of proteins. As is appreciated in the art, such hosts cannot readily be employed to produce recombinant proteins where intron-containing coding sequences such as genomic sequences are used, due to the inability of the host to faithfully process the RNA intermediate. Consequently, a broad variety of prokaryotic and eukaryotic hosts are available for genetic engineering manipulation of OMgp.

Example 2

Production of OMgp by Molecular Genetic Techniques

Where recombinant techniques are employed to produce peptides in accordance with the invention, it will be appreciated by those skilled in the art in light of the present disclosure that it may be advantageous to prepare recombinant vectors such as plasmids, bacterial phage, viruses and so forth, which incorporate recombinant DNA sequences encoding the desired amino acid sequences of OMgp, or a biologically equivalent protein or peptide. The preparation and use of such vectors which incorporate the appropriate recombinant DNA segments will be apparent to those of skill in the art in light of the disclosure herein and in light of techniques well known in the art. As used herein, the term recombinant DNA segment or insert, means any DNA segment or fragment that is inserted into a recombinant vector either for the purpose of replicating or for expressing the recombinant fragment in a recombinant host to produce the desired peptide. Preparation and use of the recombinant DNA segments offers many advantages, including among others, the ability to construct DNA segments which include peptides having sequences which correspond generally to the sequences disclosed herein (FIG. 1A, FIG. 1B, and FIG. 1C), yet have sequence modifications. This is referred to in the art as the ability to prepare so called second generation structures, for example, by site-specific mutagenesis.

Many gene transfer techniques are available to introduce genes into heterologous cells. Two of the transfer methods used successfully for this purpose are: 1) those that achieve stable integration of the cloned genes into the genome of the heterologous cells; and 2) those that produce transient expression of the cloned genes.

In the "stable integration" method, the cloned DNA segment is engineered into a plasmid under the control either of its own or a heterologous promoter. The plasmid may be cotransfected into a cell population with a second plasmid containing a selectable marker, e.g., Tn5 aminoglycoside phosphotransferase (confers resistance to the antibiotic G418). Not all cell types are amenable to these methods.

Radioimmunoassay or immunostaining procedures (well known to those skilled in the art) may be used to assay gene expression.

Alternative methods to achieve plasmid transfection employ defective, amphotrophic retroviruses. Higher transformation is possible with these methods than with those described above. Random incorporation into the genome leads to somewhat unpredictable results.

Transient gene expression systems may employ the SV40 virus as a vector, (Gryuss, et al. 1981) (Gruss, et al. 1981). Efficiency of expression varies among mammalian cell types There are size limits to the gene being transferred.

Vaccinia virus genes are transcribed in infected cells without the incorporation of foreign splicing or transport signals. This vector is useful for inter-specific gene transfer and can transfer large foreign gene inserts. Genes may also be transferred to cells via mechanical bombardment.

Example 3

Synthesis of Nucleic Acid Sequences

There are many methods well-known to those skilled in the art for synthesizing nucleic acid sequences. In the phosphotriester method, oligonucleotides are prepared and then linked to form longer segments as exemplified in the synthesis and cloning of the somatostatin gene (U.S. Pat. No. 4,356,270). The phosphodiester method of linking is also available. Neither of these methods is very efficient in terms of time and labor, for large amounts.

Oligonucleotides may be synthesized using an automated DNA synthesis machine, e.g., that of Applied Biosystems, Inc., Foster City, Calif., which uses phosphoramidite chemistry (the manufacturer provides instructions).

Example 4

Nucleic Acid Hybridization to Detect the Sequence Capable of Coding for OMgp, or its Biologically Functional Equivalent The nucleic acid sequence information provided by the invention allows for the preparation of relatively short DNA (or RNA) sequences having the ability to specifically hybridize to gene sequences of the OMgp gene. In these aspects, nucleic acid probes of an appropriate length are prepared based on a consideration of the sequence shown in FIG. 1. The ability of such nucleic acid probes to specifically hybridize to the OMgp gene sequences lends them particular utility in a variety of embodiments. Most importantly, the probes can be used in a variety of assays for detecting the presence of complementary sequences in a given sample. Other uses are envisioned, including the use of the sequence information for the preparation of mutant species primers, or primers for use in preparing other genetic constructions.

To provide certain of the advantages in accordance with the invention, the preferred nucleic acid sequence employed for hybridization studies or assays includes sequences that are complementary to at least a 14 base nucleotide stretches of the sequence shown in FIG. 1A, FIG 1B, and FIG. 1C. A size of at least 14 nucleotides in length helps to ensure that the fragment will be of sufficient length to form a duplex molecule that is both stable and selective. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production. Segments of from 18 to 22 bases are also within the scope of this invention.

Accordingly, the nucleotide sequences of the invention are important for their ability to selectively form duplex molecules with complementary stretches of the gene. Depending on the application envisioned, varying conditions of hybridization may be employed to achieve varying degree of selectivity of the probe toward the target sequence. For applications requiring a high degree of selectivity, relatively stringent conditions may be employed to form the hybrids, for example, selecting relatively low salt and/or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, preparation of mutants employing a mutant primer strand hybridized to an underlying template, or to isolate OMgp coding sequences from related species, functional equivalents, or the like, less stringent hybridization conditions are called for in order to allow formation of the heteroduplex. In these circumstances, conditions employed would be, e.g., such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred diagnostic embodiments, an enzyme tag such as urease, alkaline phosphatase or peroxidase, may be employed instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

One method of making molecules for detection of cell extracts is to use fluorescent probes. Fluorescent probes are well known to those skilled in the art. An example of a method is to bind fluorescein-labeled avidin (Vector Laboratories, Burlingame, Calif.) to a biotin-labeled protein. The signal may be enhanced.

GENERAL MATERIALS AND METHODS

Samples Used to Prepare the OMgp Protein

A. Tissue Samples

Human frontal lobes, cerebellum, and thoracic spinal cords were obtained at autopsies performed for diagnostic purposes at <24 h after the death of individuals of varying ages, all without gross or histologic evidence of neurologic disease. CNS myelin was isolated by the method of Norton and Poduslo (1973), both from human autopsy material and from fresh ovine brains obtained from a local vender. Human peripheral nerves, livers, kidneys, and spleens were also obtained at autopsies.

B. Oligodendrocyte-Myelin (OM) Protein Isolation

All steps in the isolation procedure were performed at 4° C., with the exception of the phospholipase C (PLC) incubation. Hemispheric white matter was dissected away from gray matter, homogenized 1:20 (wt/vol) in buffer (20 mM triethanolamine, 0.15M NaCl, 1 mM EDTA, 0.5 mM phenlmethylsufonyl fluoride [PMSF], pH 7.5), and centrifuged at 100,000 g for 30 min. The pellet and the supernatant were used in separate isolation pathways. The 100,000 g pellet was washed twice, and then preincubated with shaking at 37° C. for 1.5 h, whereafter it was spun down and washed twice. The pellet was again homogenized 1:20 (wt/vol), incubated with 0.5 U/ml $Bacillus\ cereus$ PLC (type III; Sigma Chemical Co., St. Louis, Mo.) for 3.5 h, and centrifuged at 100,000 g for 30 min. The PLC supernatant contained the released OMgp protein. At this point the isolation procedures of the OMgp protein from the PCL supernatant and the original white matter supernatant were identical. The OMgp protein was precipitated with ammonium sulfate at a concentration between 33 and 67% of saturation. The pellet was dissolved and dialyzed to equilibrium against buffer. A concentrated 1,000 x stock of 0.1M $CaCl_2/MnCL_2/MgCl_2$ was added to the dialysate which was then incubated for 1 h with PNA-agarose beads (Vector Laboratories, Inc., Burlingame, Calif.). The beads were packed in a disposal gravity column, washed with high salt buffer (20 mM triethanolamine, 2M NaCl, 1 mM EDTA, 0.5 mM PMSF, pH 7.5) and finally eluted with the same buffer plus 0.5M D-galactose, D-Galactose was removed from the eluates by dialysis and the dialysate was subjected to a second PNA affinity extraction. The final eluates contained highly purified OMgp protein.

C. Oligodendrocyte Isolation and Culture

Oligodendrocytes were isolated from ovine white matter and cultured as previously described (Szuchet, et al., 1980). The cultures used for the studies described here contained only (>98%) cells that stained with antibodies against galactocerebroside.

Isolation and Characterization of the OMgp Protein

A. Anion Exchange Chromatography

The protein sample (1 mg total) was applied to a MonoQ anion exchange fast protein liquid chromatograph column (Pharmacia Fine Chemicals) in 20 mM triethanolamine, pH 7.5. Proteins were eluted with a concentration gradient of NaCl at a flow of 0.2 ml/min.

B. SDS Electrophoresis, Immunoblots, and Lectin Binding

Protein samples were quantified with a Protein Assay (Bio-Rad Laboratories, Richmond, Calif.). Molecular mass standards were also from Bio-Rad Laboratories. Polypeptides were subjected to electrophoresis with the method of Fairbanks, et al. (1971) using 5.6% gels, or as described by Laemmli (1970) using 7.5 or 10% gels after solubilization in 5.7M urea. 1% (wt/vol) SDS, 1% (vol/vol) 2-mercaptoethanol, and heating at 100° C for 3 min. Gels were either directly stained with silver nitrate (Merril, et al., 1984) or the polypeptides were electrically transferred from the gels onto nitrocellulose sheets using a Transblot cell (Bio-Rad Laboratories) at 60 V for 3 h in 20 mMTris-HCl buffer (pH 7.5) with 20% (vol/vol) methanol (Towbin, et al., 1979). The nitrocellulose was quenched overnight with 5% (wt/vol) BSA in 0.15M NaCl-0.05M Tris-HCl buffer at pH 7.6 (TBS). The nitrocellulose was then washed for 15 min before a 1-h incubation with either rat polyclonal antibodies against the OMgp protein, polyclonal rabbit antibodies against N-CAM, the HNK-1 mouse monoclonal antibody, or PNA (50 µg/ml; Vector Laboratories, Inc.). In all cases except for PNA staining, 0.15M NaCl-0.05M Tris-HCl (pH 7.6) containing 0.005% (vol/vol) P-40 (Particle Data, Inc., Elmhurst, IL) and 5% (vol/vol) normal goat serum was used for all washes and dilutions, whereas 0.5% (wt/vol) BSA was substituted for goat serum in washes and dilutions for PNA staining. Sheets incubated with antibodies were washed three times for 15 min. each, incubated for 1 h with peroxidase-labeled antibodies against rat, rabbit, or mouse immunoglobulins (Dako Corp., Santa Barbara, Calif.), and then washed three times again. Alternatively, the PNA-exposed strips were washed three times and incubated with goat anti-PNA antibodies (10 µg/ml; Vector Laboratories, Inc.), and then washed three times and incubated for 1 h with peroxidase-labeled rabbit anti-goat immunoglobulins (Dako Corp.), followed by three washes. Conjugates were used at 1:100. The sheets were developed in 0.05% (wt/vol) diaminobenzidine tetrahydrochloride and 0.01% (vol/vol) $H_2O_2$ in 0.15M NaCl-0.05M Tris-HCl (pH 7.6). Various concentrations of $\alpha$-methyl-D-mannoside (Sigma Chemical Co.), D-glucose (Vector Laboratories, Inc.), or D-galactose (Vector Laboratories, Inc.) were tested for their ability to block PNA binding. The monosaccharides were present with PNA during the primary incubation period and during the first two of three subsequent washes.

C. Amino Acid Sequencing

The $NH_2$-terminal sequence of the OMgp protein was determined by automated Edman degradation using a gas-phase sequenator (model 470A; Applied Biosystems, Inc., Foster, Calif.) with an online amino acid phenylthiohydantoin analyzer. Quantitation was done with a Nelson Analytical (Cupertino, Calif.) system.

D. Enzymatic Treatments

1) Phospholipases.

Preparative release of the OMgp protein using B. cereus PLC (type II; Sigma Chemical Co.) was described above in the isolation method. To inhibit the phosphatidylcholine (PC)-specific PLC in this preparation 5mM o-phenanthroline (Sigma Chemical Co.) was used (Little, 1981), while 5 mM $Zn^{++}$ was included to inhibit the phosphatidylinositol (PI)-specific PLC (Ikezawa and Taguchi, 1981). A pure PI-specific PLC from *Bacillus thuringiensis* was used at 50 mU/ml in 50 mM Trismaleate (pH 7.4). Highly purified PC-specific PLC from *B. cereus* was also used at 10 U/ml (type I; Boehringer Mannheim Diagnostics, Inc., Houston, Tx).

2) Glycanases.

Enzymatic cleavage of both complex and high-mannose N-linked glycans by Endoglycosidase F (endo-$\beta$-N-acetylglucosaminidase F; New England Nuclear, Boston, Mass.) or only of high-mannose N-linked chains by Endoglycosidase H (endo-$\beta$-N-acetylglucosaminidase H; New England Nuclear) was done as described (Elder and Alexander, 1982; Tarentino and Maley, 1974) at 37° C. for 12 h using 5 µg of OMgp protein and 0.5 U enzyme in 100 µl total vol. Neuraminidase (type X; Sigma Chemical Co.) digestion (1 U/ml) was performed in 50 mM sodium acetate (pH 5.1) at 37° C. for 4 h. For complete deglycosylation, the OMgp protein was first treated with Endoglycosidase F as above in 100 mM sodium phosphate (pH 6.0), followed by the addition of an equal volume of 2.5% (vol/vol) NP-40 in 50 mM Tris-maleate (pH 5.6) and incubation with neuraminidase for 4 h. The final step was cleavage of O-linked glycans using 50 mU/ml of 0-glycanase (endo-$\alpha$-N-acetylgalactosaminidase; Genzyme Corp., Boston, Mass.) for 12 h.

General Recombinant DNA Technology

Restriction enzymes and enzymes used in cDNA cloning were obtained from commercial sources. $^{32}$P-labeled nucleotides were purchased from DuPont Co. (Wilmington, Del.). Preparation of plasmid DNA, restriction digestions, agarose gel electrophoresis, RNA and ENA blotting, and hybridizations were from standard protocols described by Maniatis, et al. (1982). Northern, Southern, and Western Blotting Total RNA (10 µg/lane) isolated (Chomczynski and Sacchi, 1987) from biopsied human cerebral white matter that had been quick frozen in liquid nitrogen was electrophoresed on a 1.2% (wt/vol) agarose formaldehyde gel and capillary blotted onto Gene Screen™ nylon membrane (DuPont Co.). Both Northern and Southern blots were probed with random primed $^{32}$P[dCTP] cDNA insert fragments. Blots were washed twice for 30 min. with 0.1×SSC+ 1% (wt/vol) SDS at 65° C. and exposed with intensifying screens at −80° C. OMgp isolation, SDS-PAGE on 7.5% Laemmli gels, and Western blotting were done as previously described (Mikol and Stefansson, 1988).

DNA Sequencing

Either double- or single-stranded DNA was sequenced using dideoxynucleotide termination (Sanger, et al., 1977) with Sequenase™ (United States Biochemical Corp., Cleveland, Ohio) (Tabor and Richardson, 1987). Nested deletions of selected subclones were made with exonuclease III (Henikoff, 1984) and all clones were sequenced in both directions. The sequence analysis was performed using the sequence analysis software package of the University of Wisconsin Genetics Computer Group (Devereux, et al., 1984). Polypeptide sequences were compared using the Dayhoff table and the GAP program in the above software package.

Screening of cDNA Libraries gt11 cDNA libraries from the spinal cord (catalog No. 37434) and brainstem (catalog No. 37432) of a one day old child were obtained from the American Type Culture Collection (Rockville, Md.). Polyclonal rat anti-OMgp antiserum, obtained as previously described (Mikol and Stefansson, 1988), was first preabsorbed against gt11 lysates of *Escherichia coli* and then used to probe recombinant plaques from the neonatal spinal cord cDNA library on nitrocellulose plate replicas (Snyder and Davis, 1985). The single positive cDNA clone (S1) obtained from antibody screening was used to screen all three libraries on Colony/Plaque Screen nylon membrane (DuPont Co.) plate replicas. The S1 cDNA insert used to probe the libraries was prepared from agarose gels and labeled with $^2$P[dCTP] by random priming (Feinberg and Vogelstein, 1983) using an oligo-labeling kit (Pharmacia Fine Chemicals, Piscataway, NJ). After hybridization, the nylon disks were washed twice for 30 min. with 0.1× SSC+1% (wt/vol) SDS at 65° C. and exposed with intensifying screens at −80° C. All positive clones were plaque purified and subcloned into Bluescript™ (Stratagene, LaJolla, CA) by shotgun ligation for restriction mapping and sequencing.

Antibodies

The OMgp protein (15 µg) was emulsified in complete Freund's adjuvant and injected into the footpads of female Lewis rats for each of three injections over 2 mo. Antibodies specific for the polypeptide backbone of the OMgp were affinity purified from deglycosylated protein on nitrocellulose using a previously described method (Olmsted, 1981). After absorption with isolated OMgp, the affinity-purified antibodies reacted with nothing on immunoblots of brain homogenates and gave no staining in immunohistochemistry. A hybridoma producing anti-HNK-1 antibody was obtained from the American Tissue Collection (Rockville, Md.) and polyclonal antibodies against N-CAM were generously provided by Dr. Urs Rutishauser of Case Western Reserve University, Cleveland, Ohio.

The spleens of rats that displayed significant titers against OMgp (Mikol and Stefansson, 1988) were fused with SP2/0-Ag-14 mouse myeloma cells (Galfre and Milstein, 1981). Hybridomas were screened for binding to OMgp using the Bio-Dot™ apparatus (Bio-Rad Laboratories, Richmond, Calif.) and the positive hybridomas were cloned by limiting dilution. While the majority of clones appeared to recognize carbohydrate moieties of OMgp, mAb 16 was found to be highly specific and stained OMgp that had been treated with N-glycanase (Genzyme Corp., Boston, Mass.) to remove N-linked carbohydrates.

New Zealand white female rabbits were immunized with 20 μg human OMgp in complete Freund's adjuvant (Difco Laboratories, Inc., Detroit, MI), and boosted twice at 3-wk intervals using 20 μg OMgp in incomplete Freund's adjuvant (Difco Laboratories, Inc.). Rabbit antiserum was preabsorbed against nitrocellulose plate replicas of gt11 infected E. coli lysates, and then affinity purified on S1 lysate replicas (Snyder and Davis, 1985). The mouse anti-HNK-1 mAb (Becton Dickinson & Co., Mountain View, Calif.) was used as described previously (Mikol, et al., 1988).

Immunochemistry and Immunohistochemistry

Sections (6 μm) of formalin-fixed paraffin-embedded blocks from human autopsy material and ovine brains were stained with the rat anti-OMgp protein polyclonal antiserum (1:100), preimmune rat serum (1:40), or affinity-purified polyclonal antibodies against the OMgp. Sternberger's peroxidase-antiperoxidase method (Sternberger, 1979b) was used. Rat peroxidase-antiperoxidase complexes were obtained from Sternberger-Meyer Immunocytochemicals, Inc. (Jarretsville, Md.). The cultured ovine oligodendrocytes were stained with the same antibodies as well as with antibodies against galactocerebroside using indirect immunofluorescence (Sternberger, 1979a).

In Situ Hybridization of Metaphase Chromosomes

Chromosomes are the microscopically visible entities that contain the genetic material. A DNA molecule is in each chromosome, packaged with various protein in some species, e.g. humans. Chromosomes are most readily analyzed in somatic rather than germinal cells due to easier accessibility and better morphologic resolution. Somatic cells under division (mitosis). It is at the prometaphase or metaphase stage that chromosomes are most reliably analyzed.

In normal human cells at metaphase, 46 chromosomes are visible, existing as 22 homologous pairs of autosomes, and a pair of sex chromosomes (XX=female, XY=male).

To localize specific genes or nucleotide sequences on chromosomes, labelled probes capable of hybridizing with the chromosomes at the region of complementarity, are contacted with the cell. At sites of hybridization, label may be detected.

Figure 15:
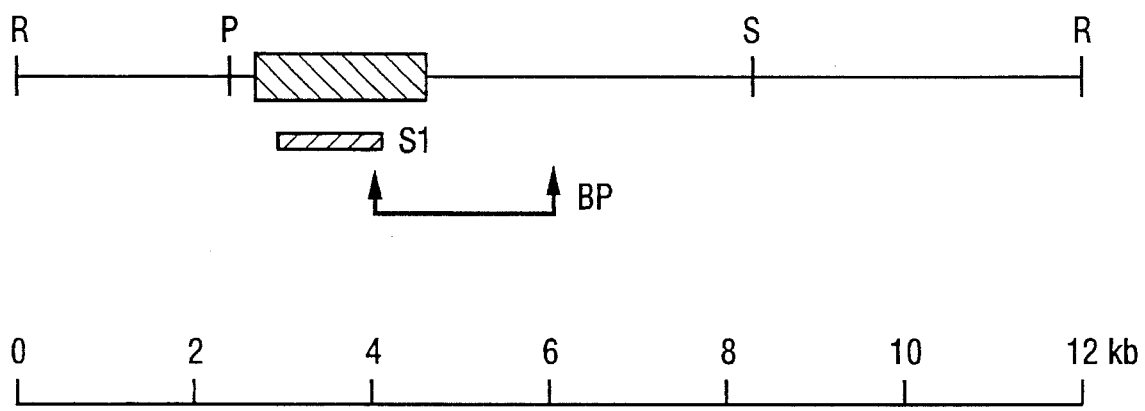
FIG. 15. A restriction map of a 12kb genomic fragment containing OMgp, (M5E10), R: EcoRI, P: PstI and S: SacI. The cross-hatched box represents the coding region and the segment corresponding to the 3' untranslated region of the OMgp message in a 5' to 3' orientation. BP marks the segment where the breakpoint (the breakpoint segment) should fall according to the Southern blot analysis.
Figure 16:
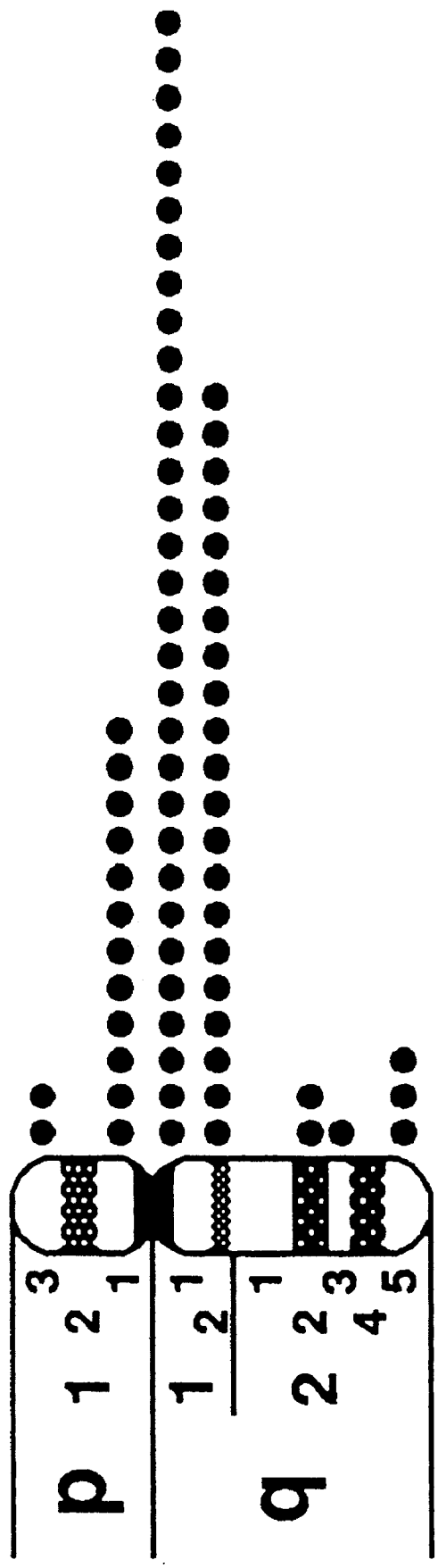
FIG. 16. Chromosomal localization of the OMgp gene is also shown to be 17 q 11.2. A radiolabelled 12 kb genomic probe (M5E10, see FIG. 17) was hybridized to the OMgp on normal human metaphase chromosomes. Each dot indicates one labeled site observed in the corresponding band. Of 100 metaphase cells examined, 37 (37%) were labeled on region p1-q1 of one or both chromosome 17 homologues. Of 266 total labeled sites observed, 72 (27.1%) were located on chromosome 17. These sites were clustered at bands p11—q12, and this cluster represented 24.1% (64/266) of all labeled sites (cumulative probability of this occurring by chance for the Poisson distribution is <<0.0005). The largest number of grains was observed at 17q11. Similar results were obtained in a second hybridization experiment using this probe. Human metaphase cells were prepared from phytohemagglutinin-stimulated peripheral blood lymphocytes (see Fisher, et al., 1989 for methods).

In an illustrative embodiment, a radiolabelled 12 kb genomic probe (M5E10) was hybridized to normal human chromosomes using methods described in Le Beau, et al., 1984. The hybridization resulted in a specific labelling only of chromosome 17, bands q11-12 (FIG. 15).

While the invention is susceptible to various modifications and alternative forms, specific embodiments thereof have been shown by way of example in the drawings and herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

REFERENCES

U.S. Pat. No. 4,356,270

Barker, D., et al. (1987). *Science*, 236: 1100–1102.
Bunge, R. P. et al. (1978). *Neurology*, 28 (Suppl) :59–67.
Chomczynski, P., and Sacchi, N. (1987). Single-step method of RNA isolation by acid guanidinium thiocyanate-phenol-chloroform extraction. *Anal. Biochem.*, 162:156–159.
Devereaux, J., et al. (1984). *Nucleic Acids Res.*, 12:387–395.
Elder, J. H., and Alexander, S. (1982). Endo-β-N-acetylglucosaminidase F: endoglycosidase from *Flavobacterium meningosepticum* that cleaves both high-mannose and complex glycoproteins. *Proc. Natl. Acad. Sci. USA*, 79:4540–4544.
Faissner, A. (1987) . *Neurosci. Lett.*, 83: 327–332.
Feinberg, A. P., and Vogelstein, B. (1983). A technique for radiolabeling DNA restriction endonuclease fragments to high specific activity. *Anal. Biochem.*, 132:6–13.
Fisher, L. W., et al. (1989). *J. Biol. Chem.*, 264:4571–4576.
Grumet, M., et al. (1985). *Proc. Natl. Acad. Sci. USA*, 82:8075–8079.
Gulcher, J. R., et al. (1986). *Proc. Natl. Acad.* Sci. USA, 83: 2118–2122.
Henikoff, S. (1984). *Gene* (Amst.), 28:351–359.
Ikezawa, H., and Taguchi, R. (1981). Phosphatidylinositol-specific phospholipase C from *Bacillus cereus* and *Bacillus thuringiensis*. Methods Enzymol., 71:731–741.
Kruse, J., et al. (1985). *Nature* (Lond.), 316: 146–148.
Kruse, J., et al. (1984). *Nature* (Lond.), 311: 153–155.
Kunemund, V., et al. (1988). *J. Cell Biol.*, 106: 213–223.
Laemmli, U. K. (1970). *Nature* (Lond.), 227:680–685.
LeBeau, M. M., et al. (1984). *Nature*, 312: 70–71.
Lees, M. B. and Brostoff, S. W., (1984). In Myelin, 2nd ed. P. Morrel, editor. Plenum Publishing Corp., New York pp. 197–224.
Lemke, G., (1988). *Neuron*, 1:535–543.
Little, C. (1981). *Method Enzymol.*, 71:725–730.
Lopez, J. A., et al. (1988). *Proc. Natl.* Acad. Sci. USA, 85:2135–2139.
Maniatis, T., et al. (1982). Molecular Cloning: A Laboratory Manual. Cold Spring Harbor Laboratory, Cold Spring Harbor, N.Y. pp. 545.
McGarry, R. C., et al. (1983). *Nature* (Lond.), 306:376–378.
Merril, C. R., et al. (1984). *Methods Enzymol.*, 104:441–447.
Mikol, D. D., et al. (1988). *J. Neurochem.*, 50:1924–1928.
Mikol, D. D., and Stefansson, K. (1988). *J. Cell Bio.*, 106:1273–1279.
Norton, W. T., and Poduslo, S. E. (1973). *J. Neurochem.*, 21:749–757.
O'Connell, P., et al. (1989). *Science*, 244:1087–1088.
Olmsted, J. B. (1981). *J. Biol. Chem.*, 256:11955–11957.
Pereira, M. E. A., et al. (1976). *Carbohydr. Res.*, 51:107–118.
Poltorak, M., et al. (1987). *J. Cell Biol.*, 105: 1893–1899.
Quarles, R. H. (1984). Dev. *Neurosci.*, 6:285–303.
Rouleau, G. A., et al. (1990). *Am. J. Human Genet.*, 46: 323–328.
Sanger, F., et al. (1977). *Proc. Natl. Acad. Sci. USA*, 74:5463–5467.
Sharon, N. and Lis, H. (1982). In The Proteins. Vol. V. 3rd ed. H. Neurath and R. L. Hill, editors. Academic Press, Inc., New York. 1–44.
Shashoua, V. E., et al. (1986). *Biochem. Biophys. Res. Commun.*, 138:902–909.
Snyder, M., and Davis R. W. (1985). Screening λgt11 expression libraries with antibody probes. In Hybridoma Technology in the Biosciences and Medicine. T. A. Springer, editor. Plenum Publishing Corp., New York. 397–406.

Snyder, M., and R. W. Davis. (1985). In Hybridoma Technology in the Biosciences and Medicine. T. A. Springer, Editor. Plenum Publishing Corp., New York, 397–406.

Sternberger, L. A. (1979a). Immunocytochemistry. John Wiley & Sons, New York. pp. 24–58.

Sternberger, L. A., (1979h). Immunocytochemistry. John Wiley & Sons, New York. pp. 104–169.

Sundler, R. et al. (1978a). Enzymatic properties of phosphatidylinositol inositolphosphohydrolase from *Bacillus cereus*. *J. Biol. Che.*, 253:4175–4179.

Sundler, R., et al. (1978b). Phospholipases as probes for membrane sidedness. *J. Biol. Chem.*, 253:5299–5304.

Szuchet, S., et al. (1980). *Brain Res.*, 200:151–164.

Tarentino, A. L., and Maley, F. (1974). Purification and properties of an indo-β-N-acetylglucosaminidase from *Streptomyces griseus*. *J. Biol. Chem.*, 249:811–817.

Thiery, J. P., et al. (1985). *J. Cell Biol.*, 100:442–456.

Towbin, H., et al. (1979). *Proc. natl. Acad. Sci. USA*, 76:4350–4354.

Tucker, G. C., et al. (1984). *Cell Differ.*, 14:223–230.

Van Vactor, D., et al. (1988). *Cell*, 52:281–290.

Vicente, V., et al. (1988). *J. Biol. Chem.*, 263:18473–18479.

Ward, K., et al. (1990). *Am. J. Human Genet.*, 46: 943–950.

What is claimed is:

1. An isolated nucleic acid that encodes the amino acid sequence set forth in FIG. 1A, FIG. 1B, and FIG. 1C and degenerate variants of said nucleic acid sequence.

2. An isolated nucleic acid that encodes OMgp (oligodendrocyte-myelin glycoprotein) having the nucleic acid sequence of FIG. 1A, FIG. 1B, and FIG. 1C.

\* \* \* \* \*